US010906942B2

(12) United States Patent
Ebert et al.

(10) Patent No.: US 10,906,942 B2
(45) Date of Patent: Feb. 2, 2021

(54) VSV/NDV HYBRID VIRUSES FOR ONCOLYTIC THERAPY OF CANCER

(71) Applicant: KLINIKUM RECHTS DER ISAR DER TECHNISCHEN UNIVERSITÄT MÜNCHEN, Munich (DE)

(72) Inventors: Oliver Ebert, Munich (DE); Jennifer Altomonte, Munich (DE)

(73) Assignee: KLINIKUM RECHTS DER ISAR DER TECHNISCHEN UNIVERSITÄT MÜNCHEN, Munich (DE)

( * ) Notice: Subject to any disclaimer, the term of this patent is extended or adjusted under 35 U.S.C. 154(b) by 28 days.

(21) Appl. No.: 16/097,748

(22) PCT Filed: May 18, 2017

(86) PCT No.: PCT/EP2017/062007
§ 371 (c)(1),
(2) Date: Oct. 30, 2018

(87) PCT Pub. No.: WO2017/198779
PCT Pub. Date: Nov. 23, 2017

(65) Prior Publication Data

US 2019/0153039 A1 May 23, 2019

(30) Foreign Application Priority Data

May 19, 2016 (EP) .................................... 16170445

(51) Int. Cl.

| | |
|---|---|
| ***C07K 14/005*** | (2006.01) |
| ***A61K 9/00*** | (2006.01) |
| ***A61K 35/766*** | (2015.01) |
| ***A61K 38/16*** | (2006.01) |
| ***A61K 38/47*** | (2006.01) |
| ***A61K 45/06*** | (2006.01) |
| ***C12N 9/24*** | (2006.01) |
| ***C12N 15/86*** | (2006.01) |
| ***A61K 38/00*** | (2006.01) |
| ***A61K 49/00*** | (2006.01) |

(52) U.S. Cl.
CPC .......... *C07K 14/005* (2013.01); *A61K 9/0019* (2013.01); *A61K 9/0021* (2013.01); *A61K 9/0085* (2013.01); *A61K 35/766* (2013.01); *A61K 38/162* (2013.01); *A61K 38/47* (2013.01); *A61K 45/06* (2013.01); *A61K 49/00* (2013.01); *C12N 9/2402* (2013.01); *C12N 15/86* (2013.01); *C12Y 302/01018* (2013.01); *A61K 38/00* (2013.01); *C07K 2319/50* (2013.01); *C07K 2319/60* (2013.01); *C12N 2760/18122* (2013.01); *C12N 2760/20232* (2013.01); *C12N 2760/20243* (2013.01); *C12N 2810/6072* (2013.01)

(58) Field of Classification Search
None
See application file for complete search history.

(56) References Cited

FOREIGN PATENT DOCUMENTS

| | | |
|---|---|---|
| WO | 2007019247 A2 | 2/2007 |
| WO | 2010040526 A1 | 4/2010 |
| WO | 2015032755 A1 | 3/2015 |

OTHER PUBLICATIONS

Altomonte, Jennifer et al. "Engineered Newcastle Disease Virus as an Improved Oncolytic Agent Against Hepatocellular Carcinoma," Molecular Therapy 18(2):275-284, Feb. 2010.
Ayala-Breton, Camilo et al. "Retargeting Vesicular Stomatitis Virus Using Measles Virus Envelope Glycoproteins," Human Gene Therapy 23:484-491, May 2012.
Ebert, Oliver et al. "Syncytia Induction Enhances the Oncolytic Potential of Vesicular Stomatitis Virus in Virotherapy for Cancer," Cancer Research 64:3265-3270, (2004).
Hastie, Eric et al. "Understanding and altering cell tropism of vesicular stomatitis virus," Virus Res. 176(0): doi:10.1016/j.virusres.2013.06.003, Sep. 2013.
Kahn, Jeffrey S. et al. "Replication-Competent or Attenuated, Nonpropagating Vesicular Stomatitis Viruses Expressing Respiratory Syncytial Virus (RSV) Antigens protect Mice Against RSV Challenge," Journal of Virology 75 (22):11079-11087, Nov. 2001.
Shinozaki, Katsunori et al. "Eradication of Advanced Hepatocellular Carcinoma in Rats via Repeated Hepatic Arterial Infusions of Recombinant VSV," Hepatology 41(1):196-203, 2005.

*Primary Examiner* — Nicole Kinsey White
(74) *Attorney, Agent, or Firm* — Saliwanchik, Lloyd & Eisenschenk

(57) ABSTRACT

The present invention relates to recombinant oncolytic viruses comprising a vesicular stomatitis virus (VSV), wherein the glycoprotein (G protein) of VSV is deleted; and which comprises a modified fusion protein (F protein) of Newcastle disease virus (NDV); and the hemagglutinin neuraminidase (HN) protein of NDV. The present invention further relates to nucleic acids encoding for the recombinant oncolytic virus and vectors comprising the nucleic acids. The present invention further relates to pharmaceutical compositions comprising the rVSV of the invention, the nucleic acid or the vector, further to uses as gene delivery tool and/or for tumor detection. The present invention further relates to the recombinant oncolytic vesicular stomatitis virus (VSV) for use in medicine, in particular for the diagnosis, prevention and/or treatment of cancer.

18 Claims, 9 Drawing Sheets

Specification includes a Sequence Listing.

Figure 1

T7
leader
N
P
M
G
L
RBZ
T7 term.
NDV/F(L289A)
NDV/HN

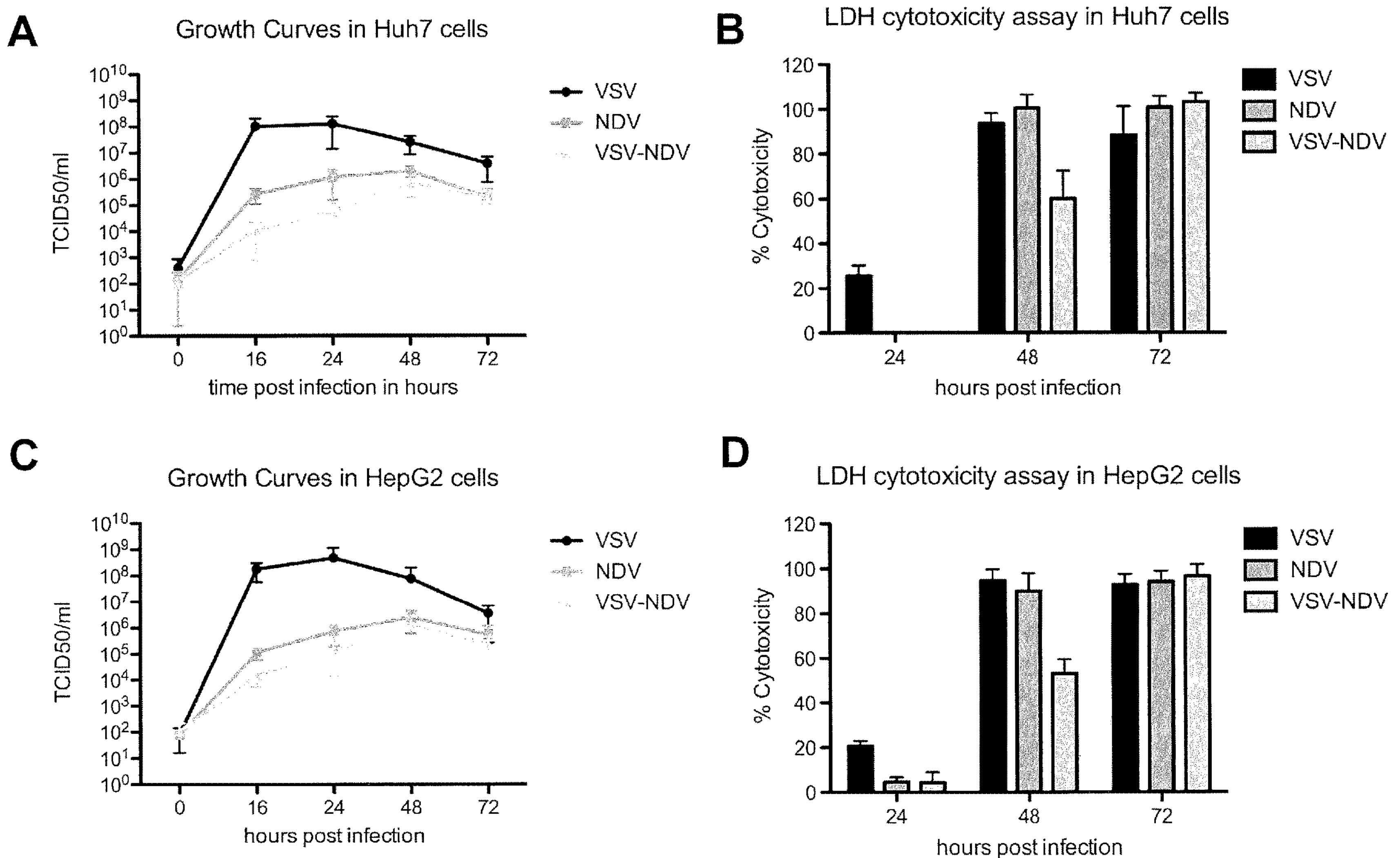

Figure 2
A
Growth Curves in Huh7 cells
TCID50/ml
$10^{10}$
$10^9$
$10^8$
$10^7$
$10^6$
$10^5$
$10^4$
$10^3$
$10^2$
$10^1$
$10^0$
0
16
24
48
72
time post infection in hours
VSV
NDV
VSV-NDV
B
LDH cytotoxicity assay in Huh7 cells
% Cytotoxicity
120
100
80
60
40
20
0
24
48
72
hours post infection
VSV
NDV
VSV-NDV
C
Growth Curves in HepG2 cells
TCID50/ml
$10^{10}$
$10^9$
$10^8$
$10^7$
$10^6$
$10^5$
$10^4$
$10^3$
$10^2$
$10^1$
$10^0$
0
16
24
48
72
hours post infection
VSV
NDV
VSV-NDV
D
LDH cytotoxicity assay in HepG2 cells
% Cytotoxicity
120
100
80
60
40
20
0
24
48
72
hours post infection
VSV
NDV
VSV-NDV Figure 5
A
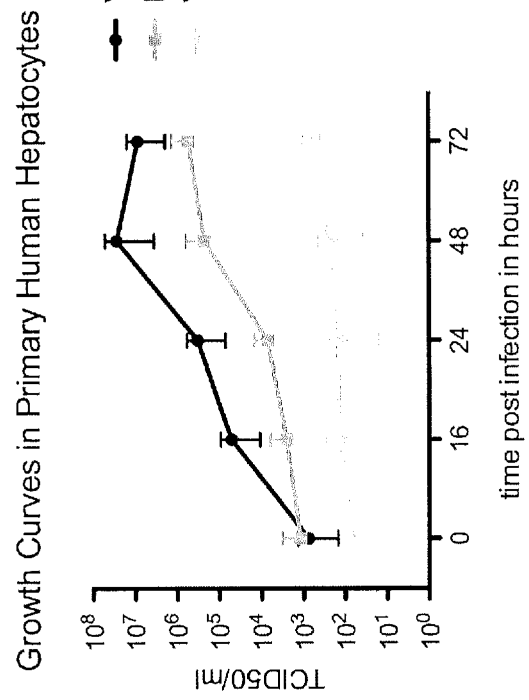
B
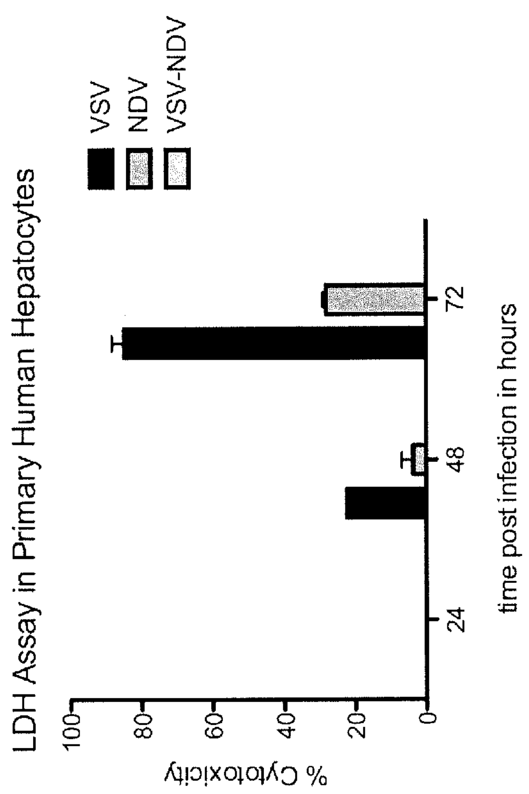

Figure 6
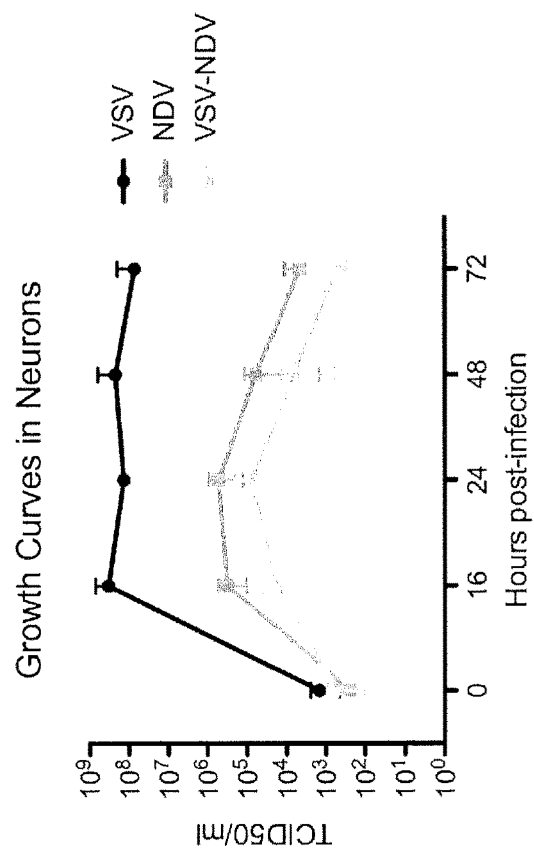
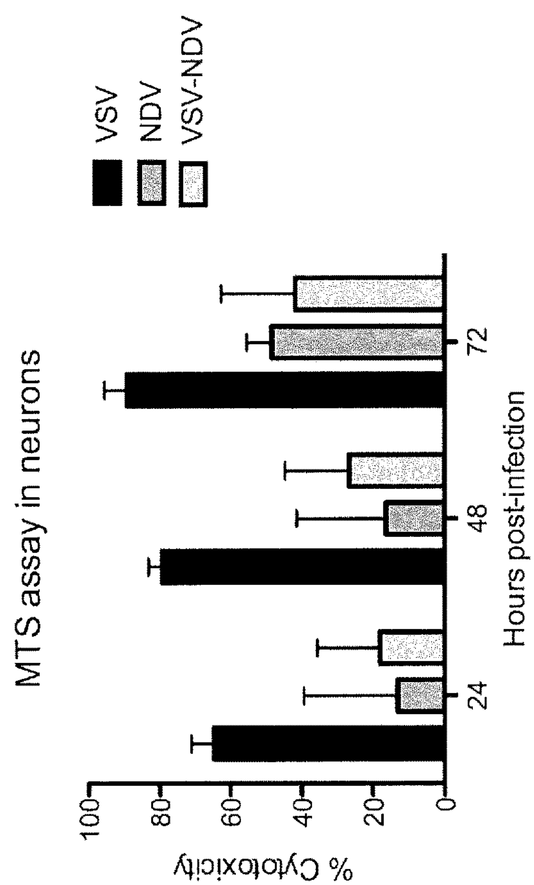

Body weight change
% Body weight
150
100
50
0
0
20
40
60
80
Time post-treamtent (days)
rVSV $10^6$
rVSV-NDV $10^6$
Viral titers in blood
$TCID_{50}$/ml
$10^4$
$10^3$
$10^2$
$10^1$
$10^0$
1
3
7
Time post-infection (hours)
rVSV $10^6$
rVSV-NDV $10^6$
Survival proportions
Percent survival
125
100
75
50
25
0
0
20
40
60
Days post-treatment
rVSV $10^6$
rVSV-NDV $10^6$

VSV/NDV HYBRID VIRUSES FOR ONCOLYTIC THERAPY OF CANCER

CROSS REFERENCE TO RELATED APPLICATIONS

This application is a National Stage Application of International Application Number PCT/EP2017/062007, filed May 18, 2017; which claims priority to European Patent Application No. 16170445.7, filed May 19, 2016.

The Sequence Listing for this application is labeled "SeqList-30Oct18-ST25.txt", which was created on Oct. 30, 2018 and is 112 KB. The entire content is incorporated herein by reference in its entirety.

The present invention relates to recombinant oncolytic viruses comprising a vesicular stomatitis virus (VSV), wherein the glycoprotein (G protein) of VSV is deleted; and which comprises a modified fusion protein (F protein) of Newcastle disease virus (NDV); and the hemagglutinin neuraminidase (HN) protein of NDV. The present invention further relates to nucleic acids encoding for the recombinant oncolytic virus and vectors comprising the nucleic acids. The present invention further relates to pharmaceutical compositions comprising the rVSV of the invention, the nucleic acid or the vector, further to uses as gene delivery tool and/or for tumor detection. The present invention further relates to the recombinant oncolytic vesicular stomatitis virus (VSV) for use in medicine, in particular for the diagnosis, prevention and/or treatment of cancer.

BACKGROUND OF THE INVENTION

Oncolytic viruses (OVs) represent a novel class of therapeutic agents for cancer treatment, due to their intrinsic ability to selectively replicate and kill tumor cells, while sparing the surrounding normal tissue (Lorence et al., 1994; Coffey et al., 1998; Kim et al., 2001; Peng et al., 2001). OV therapies involve the use of replication-competent viruses that are either inherently tumor selective or have been engineered to preferentially grow in tumor cells. During the process of malignant transformation, genetic abnormalities accumulate to provide cancer cells with growth and survival advantages. Many OVs exploit such defects in cellular signaling pathways to support their own replication in these cells. In particular, many cancer cells are impaired in their ability to secrete or respond to interferon (IFN), which is a key mechanism in the innate immune response against invading viruses in normal cells. These defects prevent tumor cells from mounting a productive antiviral defense, and, thus, replication of the OV is supported specifically in these cells.

Oncolytic viruses exert their effects both by direct killing of infected tumor cells, as well as indirect effects, such as destruction of tumor vasculature and induction of adaptive immune responses, which can be directed against the tumor and lead to destruction of neighboring uninfected tumor cells. Furthermore, genetics systems are available, which allow us to engineer and rescue recombinant viral vectors from plasmid DNA. In this way, viruses can be modified to increase tumor specificity or to express therapeutic genes and/or reporter genes.

Over the last decade, significant progress has been made in the development of enhanced OV therapies, and a variety of vectors have entered clinical trials (Kim et al., 2001; Everts and van der Poel, 2005; Patel and Kratzke, 2013). Recently, a recombinant herpes simplex virus I vector was the first oncolytic virus to be approved by the FDA for use as a clinical agent (press release Oct. 27, 2015, Amgen), and approval in Europe is expected to follow. However, in general, clinical trial results are often disappointing due to a lack of reliable and predictive preclinical models and due to inadequate tumor responses to most OV therapies in immune competent hosts.

Therapeutic efficacy of oncolytic viral therapy often comes as a trade-off with safety, such that potent vectors are often associated with toxicity, while safer viruses provide attenuated therapeutic effects. Despite promising preclinical data, the development of vesicular stomatitis virus (VSV) as a clinical agent has been substantially hampered by the fact that severe neurotoxicity has been observed in rodents and nonhuman primates in response to treatment with wild-type VSV (van den Pool et al., 2002; Johnson et al., 2007). In addition to the safety aspect, the rapid accumulation of high intratumoral titers of VSV, as a consequence of its short life cycle, results in an early and potent innate immune response, which severely limits the ability of the virus to efficiently spread and destroy the entire tumor mass before being cleared from the host (Altomonte et al., 2008).

Newcastle disease virus (NDV) has been shown to be a potent oncolytic agent with an attractive safety profile in humans; however, the use of NDV poses an environmental risk to birds and the poultry industry, as avian species are the natural hosts of the virus. Although mesogenic and velogenic strains of NDV have been shown to be the most effective as oncolytic viruses, they have been classified by the USDA as select agents since 2008, prohibiting their use and thereby severely impeding the development of NDV into a clinical agent (www.selectagents.gov).

To improve the safety of oncolytic VSV vectors, researchers have investigated a variety of approaches. First, recombinant VSVs harboring nucleotide substitutions or deletions to alter the amino acid composition of the matrix (M) protein at position 51 interfere with the ability of the endogenous M protein to inhibit cellular transcription and nucleocytoplasmic RNA transfer, allowing for antiviral cellular responses to be launched. Although these vectors have been shown to be safer than wildtype, intratumoral replication is also attenuated (Stoj dl et al., 2003; Ebert et al., 2005), limiting the therapeutic value of this approach. Another strategy to improve the safety of VSV involves the incorporation of miRNA target sequences into the virus genome in order to modify the tropism of the virus, however these vectors are also less effective (Edge et al., 2008; Kelly et al., 2010).

Various attempts are being explored to engineer the NDV genome to limit the pathogenicity in avian species, see e.g. patent application WO 2015/032755 A1. Whether or not these modifications will truly improve safety and the effect of these modifications on the oncolytic capacity of the vectors remain to be seen.

Thus, there is a need in the art for improved means and methods for oncolytic virotherapy as well as for improved oncolytic viruses.

SUMMARY OF THE INVENTION

According to the present invention this object is solved by a recombinant oncolytic virus, comprising a vesicular stomatitis virus (VSV), wherein the glycoprotein (G protein) of VSV is deleted, and which comprises a modified fusion protein (F protein) of Newcastle disease virus (NDV); and the hemagglutinin neuraminidase (HN) protein of NDV.

According to the present invention this object is solved by a nucleic acid encoding the recombinant oncolytic virus of the invention.

According to the present invention this object is solved by a vector comprising the nucleic acid of the invention.

According to the present invention this object is solved by a pharmaceutical composition, comprising (i) the recombinant oncolytic virus, the nucleic acid or the vector of the present invention; and (ii) optionally, pharmaceutically acceptable carrier(s) and/or excipient(s).

According to the present invention this object is solved by the use of the recombinant oncolytic virus, the nucleic acid or the vector of the present invention or the pharmaceutical composition of the present invention, as gene delivery tool, and/or (noninvasive) imaging of virus biodistribution, and/or for tumor detection.

According to the present invention this object is solved by providing the recombinant oncolytic virus, the nucleic acid or the vector of the present invention or the pharmaceutical composition of the present invention for use in medicine.

According to the present invention this object is solved by providing the recombinant oncolytic virus, the nucleic acid or the vector of the present invention or the pharmaceutical composition of the present invention for use in the diagnosis, prevention and/or treatment of cancer.

According to the present invention this object is solved by a method of diagnosis, prevention and/or treatment of cancer comprising the step of administering to a subject in need thereof a therapeutically effective amount of the recombinant oncolytic virus, the nucleic acid or the vector of the present invention or the pharmaceutical composition of the present invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "20 to 100 nucleotides" should be interpreted to include not only the explicitly recited values of 20 to 100, but also include individual values and sub-ranges within the indicated range. Thus, included in this numerical range are individual values such as 20, 21, 22, 23, 24, 25, 26, 27, 28, 29, . . . 97, 98, 100 and sub-ranges such as from 25 to 35, from 20 to 40, from 25 to 50, etc. This same principle applies to ranges reciting only one numerical value, such as "at least 25 nucleotides". Furthermore, such an interpretation should apply regardless of the breadth of the range or the characteristics being described.

Oncolytic Viruses and VSV Vectors

As discussed above, the present invention provides recombinant oncolytic viruses.

In particular, the present invention provides recombinant oncolytic VSV viruses wherein the glycoprotein protein of VSV is pseudotyped.

Among the most promising OV vector platforms under development are vesicular stomatitis virus (VSV) and Newcastle disease virus (NDV).

Vesicular stomatitis virus (VSV) is a negative-strand RNA virus of the Rhabdovirus family. VSV vectors are very attractive oncolytic agents due to their inherent tumor specificity and rapid replication cycle, which results in high intratumoral titers and subsequent tumor cell lysis.

The genome of VSV is a single molecule of negative-sense RNA that encodes five major proteins: glycoprotein (G), large polymerase protein (L), phosphoprotein (P), matrix protein (M) and nucleoprotein (N). The total genome is about 11,000 nucleotides.

The VSV G protein enables viral entry. It mediates viral attachment to an LDL receptor (LDLR) or an LDLR family member present on the host cell. Following binding the VSV-LDLR complex is rapidly endocytosed. It then mediates fusion of the viral envelope with the endosomal membrane. VSV enters the cell through partially clathrin-coated vesicles; virus-containing vesicles contain more clathrin and clathrin adaptor than conventional vesicles. Virus-containing vesicles recruit components of the actin machinery for their interaction, thus inducing its own uptake. Replication occurs in the cytoplasm.

The VSV L protein is encoded by half the genome, and combines with the phosphoprotein to catalyze replication of the mRNA.

The VSV M protein is encoded by an mRNA that is 831 nucleotides long and translates to a 229 amino acid-protein. The predicted M protein sequence does not contain any long hydrophobic or nonpolar domains that might promote membrane association. The protein is rich in basic amino acids and contains a highly basic amino terminal domain.

| | |
|---|---|
| VSV Indiana complete genome<br>NCBI GenBank accession No. J02428.1 | SEQ ID NO. 1 |
| VSV Indiana G protein<br>See GenBank accession No. X03633.1<br>for nucleotide and amino acid sequence. | SEQ ID NOs. 2 and 3 |

Newcastle disease virus (NDV) is an avian virus of the Paramyxovirus family. Members of this family have a single stranded linear RNA. The total genome is about 16,000 nucleotides. Replication of the virus takes place in the cytoplasm of the host cell.

It is similar to VSV in that it is a negative-stand RNA virus and has been developed as an oncolytic virus, due to its innate ability to replicate and cause lysis in tumor cells, while leaving healthy cells unharmed (Altomonte et al., 2010; Vigil et al., 2007). Phase I-II clinical trials have shown promise for NDV and suggest that there is minimal toxicity related to the therapy. A major benefit of NDV as an oncolytic agent is that the viral envelope, which is comprised of a hemagglutinin-neuraminidase (HN) and fusion (F) protein, mediates not only virus attachment and fusion to the target cell, but it causes fusion of infected cells to their neighboring uninfected cells, providing a potent mechanism for viral spread and tumor cell killing. Furthermore, new evidence indicates that the syncytia formation caused by cell-cell fusion results in a multimodal cell death response, which can synergize with the direct oncolytic effect of the virus for a potent mechanism of tumor destruction (Cuadrado-Castano et al., 2015).

Two proteins of Newcastle disease virus are inserted in the envelope. They are the haemagglutinin/neuraminidase protein (HN) and the fusion protein (F). These two proteins are important in determining the virulence of the virus and how the virus infects host cells.

The haemagglutinin/neuraminidase protein has two sections that are of interest: (1) The haemagglutinin section, which is an attachment protein and binds to receptors on the outside of the membrane of host cells including red blood cells. (2) The neuraminidase section is the active site of an enzyme that aids in the release of the virus from the membrane of host cells. The activity of this enzyme affects the time taken for the virus to elute from red blood cells.

The fusion protein F fuses the virus envelope to the membrane of the host cell. This allows penetration of the host cell by the viral genome. In order for fusion to occur, the shape of the native fusion protein must be changed. This change happens when a host cell protease cleaves the protein at a specific cleavage site. After this has happened, the fusion protein is activated and can now fuse to the membrane of the cell. The sequence of the amino acids around the cleavage site determines the range of proteases that can activate cleavage of the protein. This sequence therefore determines the virulence.

NDV F protein is responsible for viral fusion with the cell membrane and for viral spread from cell to cell via formation of syncytia. The presence of a multibasic cleavage site within the F protein allows for protein cleavage and activation by a broad range of proteases and is a determinant of virulence in velogenic viral strains.

To increase oncolytic potency of a highly attenuated lentogenic Hitchner B1 NDV strain, a polybasic cleavage site was introduced into the F protein to generate rNDV/F3aa (Vigil et al., 2007). While the resultant virus exhibited only an intermediate virulence phenotype based on a mean death time in embryonated eggs, the virus formed large syncytia and was enhanced in its replication in cancer cells, leading to enhanced oncolytic effects in various animal tumor models. Similar findings were shown when the F protein of the lentogenic NDV La Sota strain was modified in an analogous fashion (Peeters et al., 1999). The inventors have further demonstrated that a single amino acid substitution from leucine to alanine at amino acid 289 (L289A) in the F3aa-modified fusion protein results in substantially greater syncytial formation and tumor necrosis than the virus bearing only the F3aa mutation, without any additional toxicity (Altomonte et al., 2010).

The fusogenic and oncolytic activity of the rNDV/F3aa strain can be further enhanced by a point mutation in the F protein at residue 289 from leucine to alanine, generating rNDV/F3aa (L289A). In an orthotopic immunocompetent liver tumor rat model, administration of the mutant virus via hepatic arterial infusion resulted in significant syncytia formation and necrosis, which translated to a significant 20% prolongation of survival over treatment with the original rNDV/F3aa virus (Altomonte et al., 2010).

```
NDV Hitchner B1 complete genome SEQ ID NO. 4
GenBank accession No. AF375823

NDV HN protein SEQ ID NOs. 5 and 6
See GenBank accession No. AF375823 and NCBI Gene ID 912270 for nucleic acid
and amino acid sequence.

NDVF protein SEQ ID NOs. 7 and 8
See GenBank accession No. AF375823 and NCBI Gene ID 912271 for nucleic acid
and amino acid sequence.

SEQ ID NO. 8
MGSRPFTKNP APMMLTIRVA LVLSCICPAN SIDGRPFAAA GIVVTGDKAV NIYTSSQTGS   60

IIVKLLPNLP KDKEACAKAP LDAYNRTLTT LLTPLGDSIR RIQESVTTSG GGRQGRLIGA  120

IIGGVALGVA TAAQITAAAA LIQAKQNAAN ILRLKESIAA TNEAVREVTD GLSQLAVAVG  180

KMQQFVNDQF NKTAQELDCI KIAQQVGVEL NLYLTELTTV FGPQITSPAL NKLTIQALYN  240

LAGGNMDYLL TKLGIGNNQL SSLIGSGLIT GNPILYDSQT QLLGIQVTLP SVGNLNNMRA  300

TYLETLSVST TRGFASALVP KVVTQVGSVI EELDTSYCIE TDLDLYCTRI VTFPMSPGIY  360

SCLSGNTSAC MYSKTEGALT TPYMTIKGSV IANCKMTTCR CVNPPGIISQ NYGEAVSLID  420

KQSCNVLSLG GITLRLSGEF DVTYQKNISI QDSQVIITGN LDISTELGNV NNSISNALNK  480

LEESNRKLDK VNVKLTSTSA LITYIVLTII SLVFGILSLI LACYLMYKQK AQQKTLLWLG  540

NNTLDQMRAT TKM                                                     553

NDV F3aa-modified fusion protein SEQ ID NOs. 9 and 10
SEQ ID NO. 9 (Park et al., 2006 and Altomonte et al., 2010)
ATGGGCTCCAGACCTTCTACCAAGAACCCAGCACCTATGATGCTGACTATCCGGGTCGCGCTGGTACTGAGTTGC
ATCTGCCCGGCAAACTCCATTGATGGCAGGCCTCTTGCAGCTGCAGGAATTGTGGTTACAGGAGACAAAGCAGTC
AACATATACACCTCATCCCAGACAGGATCAATCATAGTTAAGCTCCTCCCGAATCTGCCCAAGGATAAGGAGGCA
TGTGCGAAAGCCCCCTTGGATGCATACAACAGGACATTGACCACTTTGCTCACCCCCCTTGGTGACTCTATCCGT
AGGATACAAGAGTCTGTGACTACATCTGGAGGGCGGAGACAGAGGCGCTTTATAGGCGCCATTATTGGCGGTGTG
GCTCTTGGGGTTGCAACTGCCGCACAAATAACAGCGGCCGCAGCTCTGATACAAGCCAAACAAAATGCTGCCAAC
```

-continued

ATCCTCCGACTTAAAGAGAGCATTGCCGCAACCAATGAGGCTGTGCATGAGGTCACTGACGGATTATCGCAACTA
GCAGTGGCAGTTGGGAAGATGCAGCAGTTTGTTAATGACCAATTTAATAAAACAGCTCAGGAATTAGACTGCATC
AAAATTGCACAGCAAGTTGGTGTAGAGCTCAACCTGTACCTAACCGAATTGACTACAGTATTCGGACCACAAATC
ACTTCACCTGCCTTAAACAAGCTGACTATTCAGGCACTTTACAATCTAGCTGGTGGGAATATGGATTACTTATTG
ACTAAGTTAGGTATAGGGAACAATCAACTCAGCTCATTAATCGOTAGCGGCTTAATCACCGGTAACCCTATTCTA
TACGACTCACAGACTCAACTCTTGGGTATACAGGTAACTCTACCTTCAGTCGGGAACCTAAATAATATGCGTGCC
ACCTACTTGGAAACCTTATCCGTAAGCACAACCAGGGGATTTGCCTCGGCACTTGTCCCAAAAGTGGTGACACAG
GTCGGTTCTGTGATAGAAGAACTTGACACCTCATACTGTATAGAAACTGACTTAGATTTATATTGTACAAGAATA
GTAACGTTCCCTATGTCCCCTGGTATTTACTCCTGCTTGAGCGGCAATACATCGGCCTGTATGTACTCAAAGACC
GAAGGCGCACTTACTACACCATATATGACTATCAAAGGCTCAGTCATCGCTAACTGCAAGATGACAACATGTAGA
TGTGTAAACCCCCCGGGTATCATATCGCAAAACTATGGAGAAGCCGTGTCTCTAATAGATAAACAATCATGCAAT
GTTTTATCCTTAGGCGGGATAACTTTAAGGCTCAGTGGGGAATTCGATGTAACTTATCAGAAGAATATCTCAATA
CAAGATTCTCAAGTAATAATAACAGGCAATCTTGATATCTCAACTGAGCTTGGGAATGTCAACAACTCGATCAGT
AATGCTTTGAATAAGTTAGAGGAAAGCAACAGAAAACTAGACAAAGTCAATGTCAAACTGACCAGCACATCTGCT
CTCATTACCTATATCGTTTTGACTATCATATCTCTTGTTTTTGGTATACTTAGCCTGATTCTAGCATGCTACCTA
ATGTACAAGCAAAAGGCGCAACAAAAGACCTTATTATGGCTTGGGAATAATACCCTAGATCAGATGAGAGCCACT
ACAAAAATGTGA

SEQ ID NO. 10 (Park et al., 2006 and Altomonte et al., 2010)

MGSRPFTKNP APMMLTIRVA LVLSCICPAN SIDGRPFAAA GIVVTGDKAV NIYTSSQTGS 60

IIVKLLPNLP KDKEACAKAP LDAYNRTLTT LLTPLGDSIR RIQESVTTSG GRRQRRFIGA 120

IIGGVALGVA TAAQITAAAA LIQAKQNAAN ILRLKESIAA TNEAVHEVTD GLSQLAVAVG 180

KMQQFVNDQF NKTAQELDCI KIAQQVGVEL NLYLTELTTV FGPQITSPAL NKLTIQALYN 240

LAGGNMDYLL TKLGIGNNQL SSLIGSGLIT GNPILYDSQT QLLGIQVTLP SVGNLNNMRA 300

TYLETLSVST TRGFASALVP KVVTQVGSVI EELDTSYCIE TDLDLYCTRI VTFPMSPGIY 360

SCLSGNTSAC MYSKTEGALT TPYMTIKGSV IANCKMTTCR CVNPPGIISQ NYGEAVSLID 420

KQSCNVLSLG GITLRLSGEF DVTYQKNISI QDSQVIITGN LDISTELGNV NNSISNALNK 480

LEESNRKLDK VNVKLTSTSA LITYIVLTII SLVFGILSLI LACYLMYKQK AQQKTLLWLG 540

NNTLDQMRAT TKM

NDV F3aa-modified fusion protein with L289A SEQ ID NOs. 11 and 12

SEQ ID NO. 11 (See also Altomonte et al., 2010)

ATGGGCTCCAGACCTTCTACCAAGAACCCAGCACCTATGATGCTGACTATCCGGGTCGCGCTGGTACTGAGTTGC
ATCTGCCCGGCAAACTCCATTGATGGCAGGCCTCTTGCAGCTGCAGGAATTGTGGTTACAGGAGACAAAGCAGTC
AACATATACACCTCATCCCAGACAGGATCAATCATAGTTAAGCTCCTCCCGAATCTGCCCAAGGATAAGGAGGCA
TGTGCGAAAGCCCCCTTGGATGCATACAACAGGACATTGACCACTTTGCTCACCCCCCTTGGTGACTCTATCCGT
AGGATACAAGAGTCTGTGACTACATCTGGAGGGCGGAGACAGAGGCGCTTTATAGGCGCCATTATTGGCGGTGTG
GCTCTTGGGGTTGCAACTGCCGCACAAATAACAGCGGCCGCAGCTCTGATACAAGCCAAACAAAATGCTGCCAAC
ATCCTCCGACTTAAAGAGAGCATTGCCGCAACCAATGAGGCTGTGCATGAGGTCACTGACGGATTATCGCAACTA
GCAGTGGCAGTTGGGAAGATGCAGCAGTTTGTTAATGACCAATTTAATAAAACAGCTCAGGAATTAGACTGCATC
AAAATTGCACAGCAAGTTGGTGTAGAGCTCAACCTGTACCTAACCGAATTGACTACAGTATTCGGACCACAAATC
ACTTCACCTGCCTTAAACAAGCTGACTATTCAGGCACTTTACAATCTAGCTGGTGGGAATATGGATTACTTATTG
ACTAAGTTAGGTATAGGGAACAATCAACTCAGCTCATTAATCGGTAGCGGCTTAATCACCGGTAACCCTATTCTA
TACGACTCACAGACTCAACTCTTGGGTATACAGGTAACTGCACCTTCAGTCGGGAACCTAAATAATATGCGTGCC
ACCTACTTGGAAACCTTATCCGTAAGCACAACCAGGGGATTTGCCTCGGCACTTGTCCCAAAAGTGGTGACACAG
GTCGGTTCTGTGATAGAAGAACTTGACACCTCATACTGTATAGAAACTGACTTAGATTTATATTGTACAAGAATA
GTAACGTTCCCTATGTCCCCTGGTATTTACTCCTGCTTGAGCGGCAATACATCGGCCTGTATGTACTCAAAGACC
GAAGGCGCACTTACTACACCATATATGACTATCAAAGGCTCAGTCATCGCTAACTGCAAGATGACAACATGTAGA
TGTGTAAACCCCCCGGGTATCATATCGCAAAACTATGGAGAAGCCGTGTCTCTAATAGATAAACAATCATGCAAT
GTTTTATCCTTAGGCGGGATAACTTTAAGGCTCAGTGGGGAATTCGATGTAACTTATCAGAAGAATATCTCAATA
CAAGATTCTCAAGTAATAATAACAGGCAATCTTGATATCTCAACTGAGCTTGGGAATGTCAACAACTCGATCAGT
AATGCTTTGAATAAGTTAGAGGAAAGCAACAGAAAACTAGACAAAGTCAATGTCAAACTGACCAGCACATCTGCT
CTCATTACCTATATCGTTTTGACTATCATATCTCTTGTTTTTGGTATACTTAGCCTGATTCTAGCATGCTACCTA
ATGTACAAGCAAAAGGCGCAACAAAAGACCTTATTATGGCTTGGGAATAATACCCTAGATCAGATGAGAGCCACT
ACAAAAATGTGA

SEQ ID NO. 12 (See also Altomonte et al., 2010)

MGSRPFTKNP APMMLTIRVA LVLSCICPAN SIDGRPFAAA GIVVTGDKAV NIYTSSQTGS 60

IIVKLLPNLP KDKEACAKAP LDAYNRTLTT LLTPLGDSIR RIQESVTTSG GRRQRRFIGA 120

IIGGVALGVA TAAQITAAAA LIQAKQNAAN ILRLKESIAA TNEAVHEVTD GLSQLAVAVG 180

KMQQFVNDQF NKTAQELDCI KIAQQVGVEL NLYLTELTTV FGPQITSPAL NKLTIQALYN 240

LAGGNMDYLL TKLGIGNNQL SSLIGSGLIT GNPILYDSQT QLLGIQVTAP SVGNLNNMRA 300

TYLETLSVST TRGFASALVP KVVTQVGSVI EELDTSYCIE TDLDLYCTRI VTFPMSPGIY 360

-continued

```
SCLSGNTSAC MYSKTEGALT TPYMTIKGSV IANCKMTTCR CVNPPGIISQ NYGEAVSLID 420

KQSCNVLSLG GITLRLSGEF DVTYQKNISI QDSQVIITGN LDISTELGNV NNSISNALNK 480

LEESNRKLDK VNVKLTSTSA LITYIVLTII SLVFGILSLI LACYLMYKQK AQQKTLLWLG 540

NNTLDQMRAT TKM                                                    553
```

As discussed above, the present invention provides recombinant oncolytic VSV viruses, wherein the glycoprotein protein of VSV is pseudotyped.

Recently, the concept of exchanging the glycoprotein ("pseudotyping") of a virus with that of a heterologous virus has been demonstrated as an effective means of altering virus tropism. Using this approach, the viral backbone is kept intact, and therefore, it is hypothesized that virus replication in susceptible cells should be minimally effected. One group has described a VSV vector that has been pseudotyped with the envelope protein of the lymphocytic choriomemingitis virus (LCMV-GP), which has been shown to be significantly less neurotropic than the wildtype vector (Muik et al., 2011). Similarly, the VSV glycoprotein has been exchanged with that of measles virus and modified with single-chain variable antibody fragments to retarget VSV to cancer cells expressing discrete surface receptors (Ayala-Breton et al., 2012).

In the present invention a recombinant oncolytic virus is provided, comprising a vesicular stomatitis virus (VSV),
wherein the glycoprotein (G protein) of VSV is deleted, and which comprises
a modified fusion protein (F protein) of Newcastle disease virus (NDV); and
the hemagglutinin neuraminidase (HN) protein of NDV.

In a preferred embodiment, the modified fusion protein (F protein) of NDV is the F3aa-modified F protein,
and/or comprises at least one amino acid substitution in the protease cleavage site,
preferably in position L289, e.g. L289A.

In a preferred embodiment, the G protein of VSV is replaced by the modified fusion protein and HN protein of NDV.

The recombinant oncolytic virus furthermore comprises the remaining proteins of VSV, namely the large polymerase protein (L), phosphoprotein (P), matrix protein (M) and nucleoprotein (N).

For example, the endogenous glycoprotein of VSV can be deleted from a plasmid encoding the full-length VSV genome. The NDV glycoprotein, comprising a modified fusion protein (NDV/F(L289A)) and hemagglutinin-neuraminidase (NDV/HN), can be inserted as discrete transcription units between the VSV matrix (M) and large polymerase (L) genes. See e.g. FIG. 1.

In an embodiment of the rVSV (vector) of the present invention, the modified fusion protein (F protein) of NDV comprises or consists of the amino acid sequence of SEQ ID NO. 10 [=aa sequence of F3aa protein] or SEQ ID NO. 12 [=aa sequence of F3aa protein/L289A], or an amino acid sequence having at least 60%, or preferably at least 70% or 80% or 90% or 95% sequence identity to the amino acid sequence of SEQ ID NOs. 10 or 12,
and/or wherein the modified fusion protein (F protein) of NDV is encoded by a nucleotide sequence of SEQ ID NO. 9 [=nucleotide sequence of F3aa protein] or SEQ ID NO. 11[=nucleotide sequence of F3aa protein/L289A],
or a nucleotide sequence having at least 60%, or preferably at least 70% or 80% or 90% or 95% sequence identity to the nucleotide sequence of SEQ ID NOs. 9 or 11.

In an embodiment of the rVSV (vector) of the present invention, wherein the HN protein of NDV comprises or consists of the amino acid sequence of SEQ ID NO. 6,
or an amino acid sequence having at least 60%, or preferably at least 70% or 80% or 90% or 95% sequence identity to the amino acid sequence of SEQ ID NO. 6,
and/or wherein the FIN protein of NDV is encoded by a nucleotide sequence of SEQ ID NO, 5 or a nucleotide sequence having at least 60%, or preferably at least 70% or 80% or 90% or 95% sequence identity to the nucleotide sequence of SEQ ID NO. 5.

As discussed above, the present invention comprises nucleic acids encoding the oncolytic viruses of the present invention.

As discussed above, the present invention comprises vectors comprising the nucleic acids of the present invention.

In preferred embodiments, the vector of the present invention further comprises:

reporter gene(s),
such as HSV1-sr39TK, the sodium iodide symporter (NIS), somatostatin receptor 2 (SSTR2), luciferase (Firefly or *Renilla*), green fluorescence protein (GFP), lacZ; tyrosinase
gene(s) to be delivered to target cell(s) or tissue,
such as gene(s) to be delivered to tumor cell(s) or tumor(s), e.g.
immune stimulating genes, such as IFN-$\alpha$, IFN-$\beta$, or granulocyte macrophage colony-stimulating factor (GM-CSF);
immune checkpoint inhibitory antibodies, such as PD-1, PD1-L, CTLA-4, LAG-3, or B7-1-13; and/or
tumor associated antigens (TAA) for vaccination (specific for the tumor being targeted);
or combinations thereof.

In an embodiment, the nucleic acid or the vector of the present invention comprises or consists of the nucleotide sequence of SEQ ID NO. 13 [=nucleotide sequence of complete virus/vector construct],
or a nucleotide sequence having at least 60%, or preferably at least 70% or 80% or 90% or 95% sequence identity to the nucleotide sequence of SEQ ID NO. 13,
and/or comprises or consists of the nucleotide sequence coding for an amino acid sequence with SEQ ID NOs. 6, 12, 14 to 17 [=aa sequence of the proteins encoded by the virus/vector construct],
or a nucleotide sequence having at least 60%, or preferably at least 70% or 80% or 90% or 95% sequence identity to the nucleotide sequence coding for an amino acid sequence with SEQ ID NOs. 6, 12, 14 to 17.

SEQ ID NO. 13 shows the nucleotide sequence of complete virus/vector construct.

SEQ ID Nos. 14-17 and 12 and 6 show the amino acid sequences of the proteins encoded by SEQ ID NO. 13, namely:

| | |
|---|---|
| SEQ ID NO. 14 | amino acid sequence of the protein VSV-N; |
| SEQ ID NO. 15 | amino acid sequence of the protein VSV-P; |
| SEQ ID NO. 16 | amino acid sequence of the protein VSV-M; |
| SEQ ID NO. 12 | amino acid sequence of the protein NDV-F3aa(L289A); |
| SEQ ID NO. 6 | amino acid sequence of the protein NDV-HN; |
| SEQ ID NO. 17 | amino acid sequence of the protein VSV-L. |

Pharmaceutical Compositions

As discussed above, the present invention provides a pharmaceutical composition, comprising (i) the recombinant oncolytic virus of the present invention or a nucleic acid of the present invention or a vector of the present invention; and (ii) optionally, pharmaceutically acceptable carrier(s) and/or excipient(s).

In one embodiment, the pharmaceutical composition comprises further drug(s), such as chemotherapeutic agent(s),
radiotherapeutic agent(s),
tumor vaccine(s),
immune checkpoint inhibitor(s),
cell carrier system(s),
small molecule inhibitor(s),
embolization agent(s),
shielding polymer(s).

In one embodiment, the pharmaceutical composition is formulated for systemic delivery, tumor injection, intravenous administration, intra-arterial administration, and/or for intradermal, subcutaneous, intramuscular, intravenous, intraosseous, intraperitoneal, intrathecal, epidural, intracardiac, intraarticular, intracavernous, intracerebral, intracerebroventricular and intravitreal injection(s).

Uses as Gene Delivery Tool and/or for Tumor Detection

As discussed above, the present invention provides the use of the recombinant oncolytic virus, the nucleic acid or the vector of the present invention or the phaimaceutical composition of the present invention:

as gene delivery tool and/or (noninvasive) imaging of virus biodistribution and/or for tumor detection.

In an embodiment, the vectors of the present invention comprise gene(s) to be delivered to target cell(s) or tissue, such as gene(s) to be delivered to tumor cell(s) or tumor(s), e.g.

immune stimulating genes, such as IFN-α, IFN-β, or granulocyte macrophage colony-stimulating factor (GM-CSF);

immune checkpoint inhibitory antibodies, such as PD-1, PD1-L, CTLA-4, LAG-3, or B7-H3; and/or tumor associated antigens (TAA) for vaccination (specific for the tumor being targeted).

In an embodiment, the vectors of the present invention comprise reporter gene(s), such as HSV1-sr39TK, the sodium iodide symporter (NIS), somatostatin receptor 2 (SSTR2), luciferase (Firefly or *Renilla*), green fluorescence protein (GFP), lacZ, tyrosinase and are then suitable for e.g. noninvasive imaging of virus biodistribution or tumor detection.

Medical Uses

As discussed above, the present invention provides the recombinant oncolytic viruses, the nucleic acids or the vectors of the present invention or the pharmaceutical composition of the present invention for use in medicine.

As discussed above, the present invention provides the recombinant oncolytic viruses, the nucleic acids or the vectors of the present invention or the pharmaceutical composition of the present invention for use in the diagnosis, prevention and/or treatment of cancer.

In one embodiment, the present invention provides the recombinant oncolytic viruses, the nucleic acids or the vectors of the present invention or the pharmaceutical composition of the present invention for use in oncolytic therapy.

The term "oncolytic virotherapy" as used herein refers to therapy of cancer by administration of oncolytic viruses, nucleic acids encoding them or respective vectors to induce tumor regression.

In one embodiment, the recombinant oncolytic viruses, the nucleic acids or the vectors of the present invention or the pharmaceutical composition of the present invention are provided for use in combination with other therapies.

Said other therapies can be:

cell carrier systems, e.g. T cells, dendritic cells, NK cells, mesenchymal stem cells, immunotherapies, e.g. tumor vaccines or immune checkpoint inhibitors, and/or standard tumor therapies, e.g. radiofrequency ablation, chemotherapy, embolization, small molecule inhibitors.

In one embodiment, the administration is systemic, intravenous, intra-arterial, via injection into tumor, and/or via intradermal, subcutaneous, intramuscular, intravenous, intraosseous, intraperitoneal, intrathecal, epidural, intracardiac, intraarticular, intracavernous, intracerebral, intracerebroventricular and intravitreal injection(s).

Methods of Diagnosis, Prevention and/or Treatment of Cancer

As discussed above, the present invention provides a method of diagnosis, prevention and/or treatment of cancer comprising the step of administering to a subject in need thereof a therapeutically effective amount of the recombinant oncolytic virus, the nucleic acid or the vector of the present invention or the pharmaceutical composition of the present invention.

A therapeutically effective amount of a recombinant oncolytic virus, nucleic acid or vector of the present invention is the amount which results in the desired therapeutic result, in particular tumor regression.

The recombinant viruses, nucleic acids, vectors or their pharmaceutical composition(s) are preferably administered in multiple cycles over a period of time, such as for several days up to several weeks.

In one embodiment, the administration is systemic, intravenous, intra-arterial, via injection into tumor, and/or via intradermal, subcutaneous, intramuscular, intravenous, intraosseous, intraperitoneal, intrathecal, epidural, intracardiac, intraarticular, intracavernous, intracerebral, intracerebroventricular and intravitreal injection(s).

In one embodiment, the recombinant oncolytic virus, nucleic acid or vector of the present invention or the pharmaceutical composition of the present invention are provided are administered to a subject in need thereof in combination with other therapies.

Said other therapies can be:

cell carrier systems, e.g. T cells, dendritic cells, NK cells, mesenchymal stem cells, immunotherapies, e.g. tumor vaccines or immune checkpoint inhibitors, and/or standard tumor therapies, e.g. radiofrequency ablation, chemotherapy, embolization, small molecule inhibitors, Further Description of Preferred Embodiments The invention discloses a pseudotyped VSV vector, in which the endogenous glycoprotein has been deleted and exchanged with modified envelope proteins of Newcastle disease virus (NDV).

It has previously been demonstrated that a modification of the fusion protein of the Hitchner B1 strain of NDV by introduction of a polybasic protease cleavage site (rNDV/F3aa), allows for efficient syncytia formation in a wide range of cells in the absence of exogenous proteases (Vigil et al., 2007). We have further demonstrated that a single amino acid substitution from leucine to alanine at amino acid 289 (L289A) in the F3aa-modified fusion protein results in substantially greater syncytial formation and tumor necrosis than the virus bearing only the F3aa mutation, without any additional toxicity (Altomonte et al., 2010).

According to the present invention, said modified hyperfusogenic F protein has been inserted, together with the NDV HN attachment protein, into the VSV G-deleted vector.

By creating a hybrid of these two potent oncolytic vectors, we merge the positive features of each virus, while simultaneously eliminating the safety concerns of each.

The resulting vector has the VSV backbone and, therefore, maintains the rapid replication cycle of wildtype VSV. Furthermore, due to the incorporation of the FIN and hyperfusogenic F proteins of NDV, the recombinant virus induces enhanced syncytia formation, allowing for efficient intratumoral spread of the virus and a potent mechanism of tumor cell death and induction of antitumor immune responses. Using this strategy, the benefit of a fusogenic virus can be achieved without the environmental threat associated with NDV.

Additionally, since the endogenous VSV glycoprotein has been deleted, there should be no neurotoxicity associated with the vector. Finally, since NDV attaches to target cells via sialic acid residues, which are upregulated on tumor cells (Bull et al., 2014), we can achieve additional transductional tumor targeting with the pseudotyped vector.

Although numerous pseudotyped VSV vectors have already been reported as safer vectors than wildtype VSV, our specific virus modification differs in that the substitution of the VSV envelope protein with that of NDV results in a more potent virus, in addition to being safer.

Furthermore, we introduce a mutated version of the NDV F protein for further improving the efficacy of the resulting recombinant virus, without negatively impacting safety.

The benefit of this glycoprotein exchange is three-fold:

1. The neurotropism associated with the endogenous VSV glycoprotein can be averted by the deletion of the VSV envelope and the introduction of the non-neurotropic NDV envelope proteins;
2. Tumor cells can be targeted via upregulation of sialic acid residues, which are the natural receptor for NDV; and
3. Viral spread and tumor cell killing can be significantly enhanced via introduction of the highly fusogenic mutant version of the NDV F protein.

Our construct simultaneously provides both improved safety and efficacy.

The pseudotyped virus of the present invention offers improved safety and enhanced efficacy as obvious advantages over wildtype vectors.

Furthermore, there are also advantages of this particular vector over the previously reported pseudotyped VSV vectors. Although the VSV-GP vector (pseudotyped with LCMV-GP) demonstrates an enhanced safety profile, there is no additional therapeutic mechanism afforded by the LCMV glycoprotein in comparison with that of NDV (Muik et al., 2011). Although measles virus (MV) is similar to NDV in that it is a member of the paramyxovirus family, and its envelope also consists of a hemagglutinin and fusion protein, the rVSV-MV vector (Ayala-Breton et al., 2012) does not contain any modification to increase fusigenicity, and it likely is less efficient than our hyperfusogenic VSV-NDV in syncytial formation. Furthermore, MV attaches to target cells via three discrete receptors: CD46, signal lymphocyte activation molecule (SLAM), and nectin4. However, infection of SLAM-positive immune cells leads to immunosuppression, and infection of nectin4-positive airway epithelial cells results in respiratory shedding and virus transmission, both of which would be undesirable side effects of oncolytic virus therapy. Therefore, modifications to ablate the interaction of MV H with SLAM and nectin4 (Liu et al., 2014) or to retarget the attachment protein to tumor specific receptors (Ayala-Breton et al., 2012) has been performed in the context of the rVSV-MV vectors as strategies to retarget the pseudotyped virus to the tumor. However, these restrictions to the natural attachment mechanism of the MV envelope will surely result in an attenuation of the recombinant virus. Indeed, nectin4 and CD46 have substantially overlapping receptor binding surfaces on MV H, and it was shown that disruption of nectin4 binding compromised attachment to CD46, resulting in a greatly diminished oncolytic effect (Liu et al., 2014). Finally, since the majority of the human population is vaccinated against measles virus, the high levels of circulating antibodies directed at the viral envelope will likely play a role in neutralizing the rVSV-MV vectors.

Therefore, our rVSV-NDV vector is superior to the previously reported pseudotyped vectors, due to its hyperfusogenic feature, lack of pre-existing immunity in the general population, and no expected attenuation compared to VSV or NDV.

The following examples and drawings illustrate the present invention without, however, limiting the same thereto.

BRIEF DESCRIPTION OF THE DRAWINGS

FIG. 1. Recombinant pseudotyped VSV construct expressing the glycoprotein of NDV.

The endogenous glycoprotein of VSV was deleted from a plasmid encoding the full-length VSV genome. The NDV glycoprotein, comprising a modified fusion protein (NDV/F(L289A)) and hemagglutinin-neuraminidase (NDV/HN), was inserted as discrete transcription units between the VSV matrix (M) and large polymerase (L) genes. The respective pseudotyped VSV vector was rescued using an established reverse-genetics system.

FIG. 2. rVSV-NDV can replicate in HCC cell lines and cause complete cytotoxicity.

Human HCC cell lines Huh7 (A, B) and HepG2 (C, D) were infected with a multiplicity of infection (MOI) of 0.01 of rVSV, rNDV, or rVSV-NDV. After a 1 hour infection, the cells were washed and fresh medium was added to the cells. At various time-points post-infection aliquots of the supernatant were collected for cytotoxicity measurements by LDH assay (B, D) and cell monolayers were lysed for measurements of intracellular titers by TCID50 assay (A, C). Experiments were performed in triplicate, and data are presented as mean+/−standard deviation.

Figure 3:
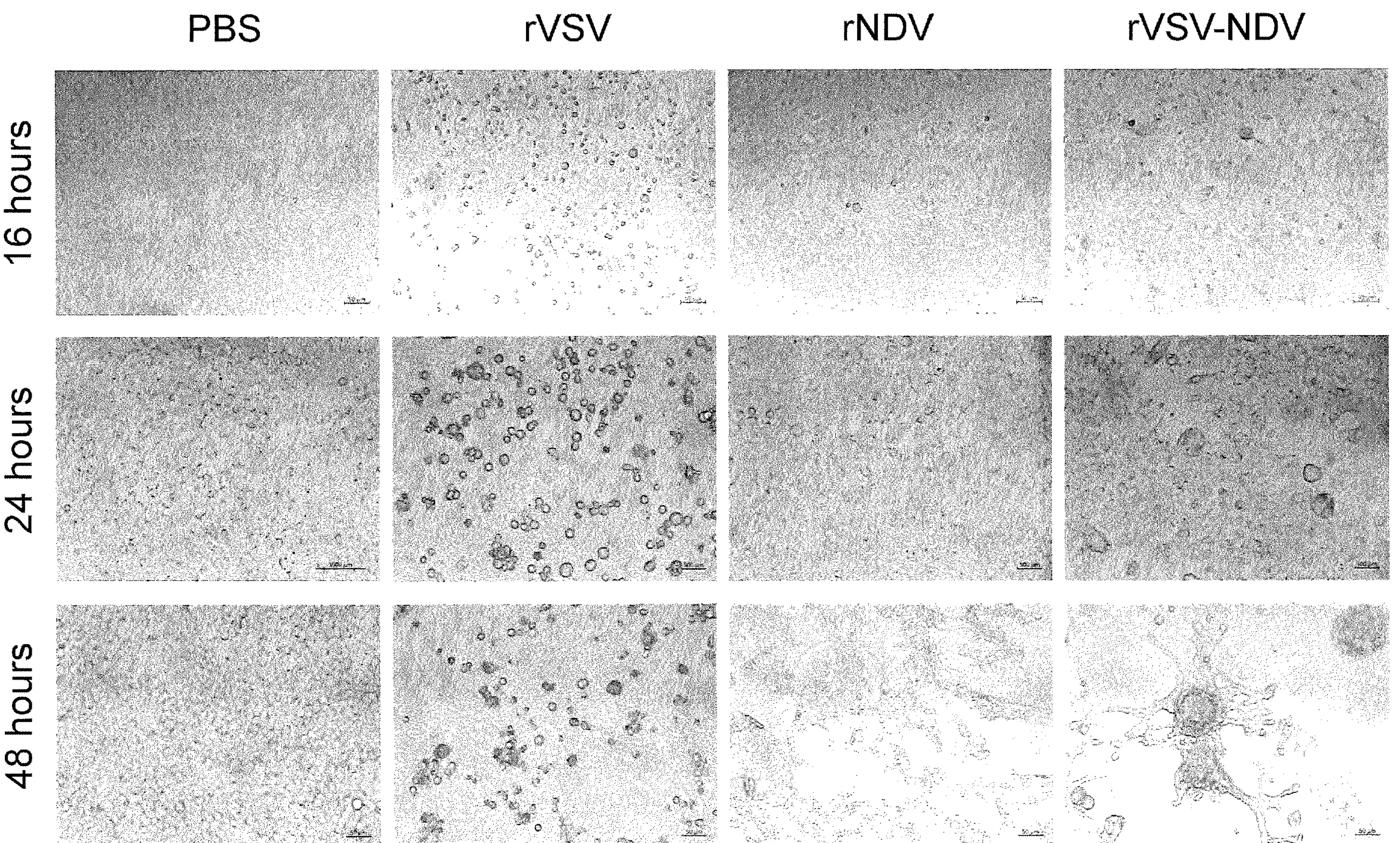

FIG. 3. rVSV-NDV infection leads to rapid syncytia formation in HCC cells.

In order to assess the ability of the pseudotyped rVSV-NDV vector to induce syncytia formation in tumor cells, various HCC cell lines were infected with rVSV-NDV, rNDV, or rVSV at an MOI of 0.01, and observed microscopically at various time-points post-infection. Additional cells were treated with PBS as a control. Huh7 cells are shown as a representative human HCC cell line, and representative images were captured under 200× magnification.

Figure 4:
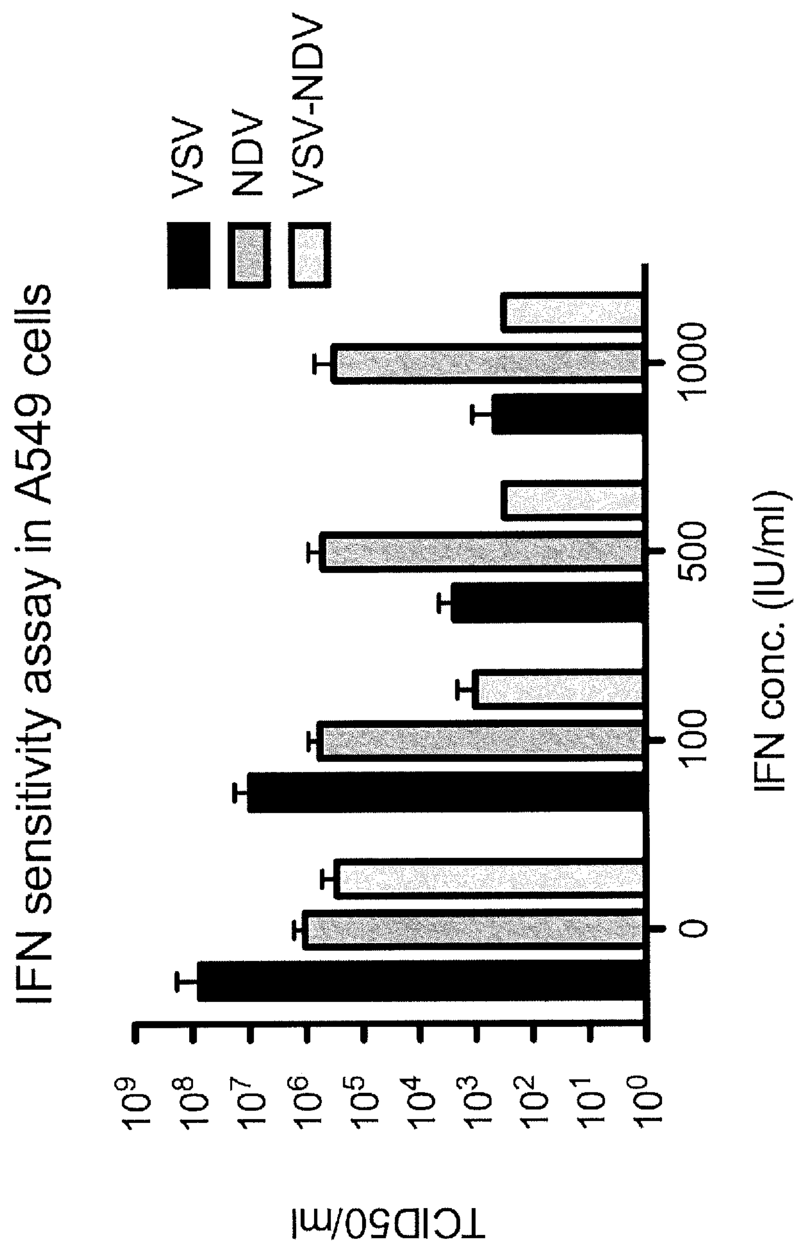

FIG. 4. Pseudotyping VSV with NDV envelope proteins does not alter the sensitivity of the vector to the antiviral actions of IFN.

To assess the sensitivity of rVSV-NDV to type I IFN, an IFN-sensitive cell line (A549) was infected with rVSV-NDV, rVSV, and rNDV at an MOI of 0.01. Cells were lysed at 48 hours post-infection, and intracellular viral titers were measured by TCID50 assay. Experiments were performed in triplicate, and mean values+/−standard deviation are shown.

FIG. 5. Replication and cytotoxicity of rVSV-NDV is substantially diminished in primary human hepatocytes.

Primary human hepatocytes were infected at an MOI of 0.01 with rVSV, rNDV, or rVSV-NDV. Cell lysates were subjected to TCID50 analysis of intracellular virus titers at various timepoints. Additionally, aliquots of supernatant were collected at various timepoints for cytotoxicity measurements by LDH assay. Experiments were performed in duplicate, and means+/−standard deviation are shown.

FIG. 6. Replication and cytotoxicity of rVSV-NDV is substantially diminished in primary mouse neurons.

Primary mouse neurons were infected at an MOI of 0.01 with rVSV, rNDV, or rVSV-NDV. Cell lysates were subjected to TCID50 analysis of intracellular virus titers at various timepoints. Additional wells were assayed for cell viability using a standard MTS assay. Experiments were performed in duplicate, and means+/−standard deviation are shown.

Figure 7:
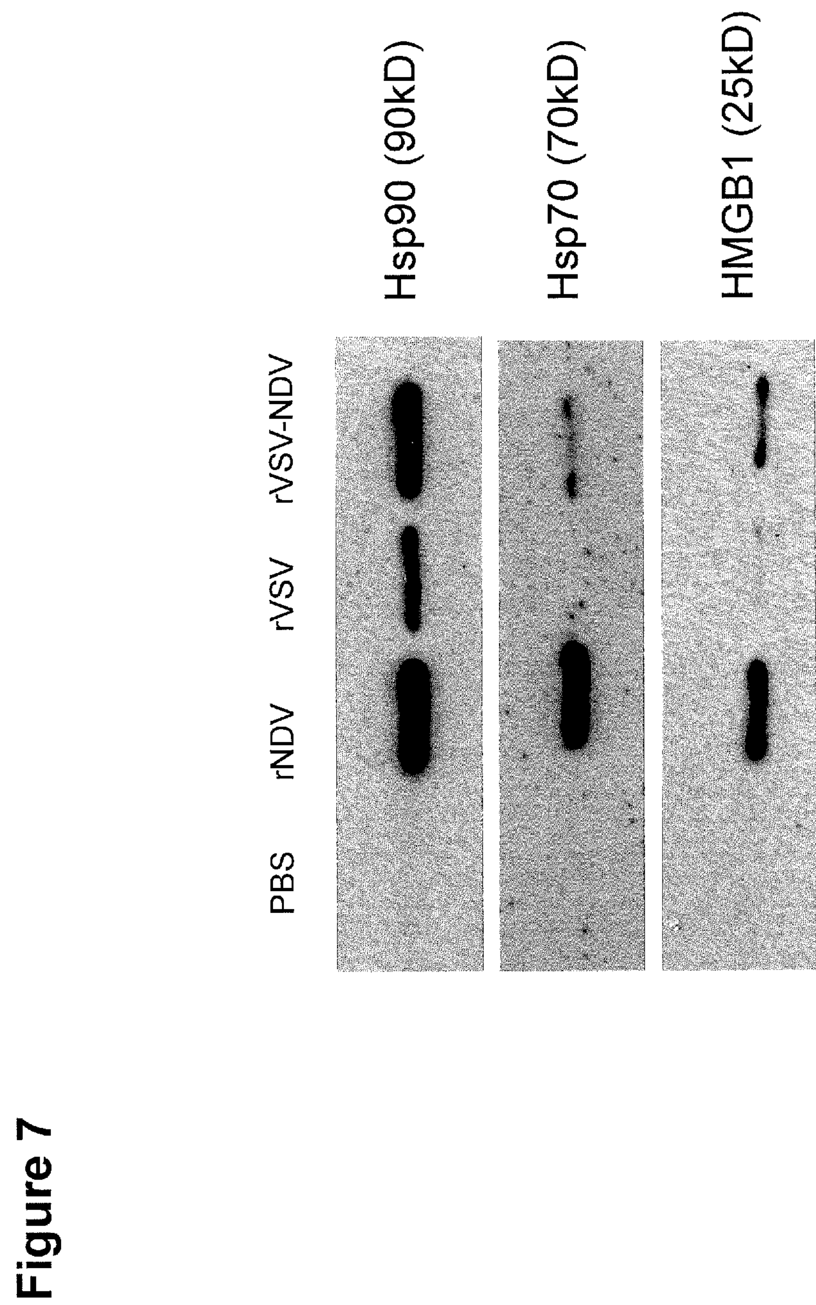

FIG. 7. The pseudotyped rVSV-NDV vector causes immunogenic cell death.

Huh7 cells were infected with rVSV, rNDV, or rVSV-NDV at an MOI of 0.01 or mock-infected for 48 hours. The conditioned media were concentrated, and 10 μg of protein were subjected to Western blot analysis for detection of released HMGB1, Hsp70, and Hsp90.

Figure 8:
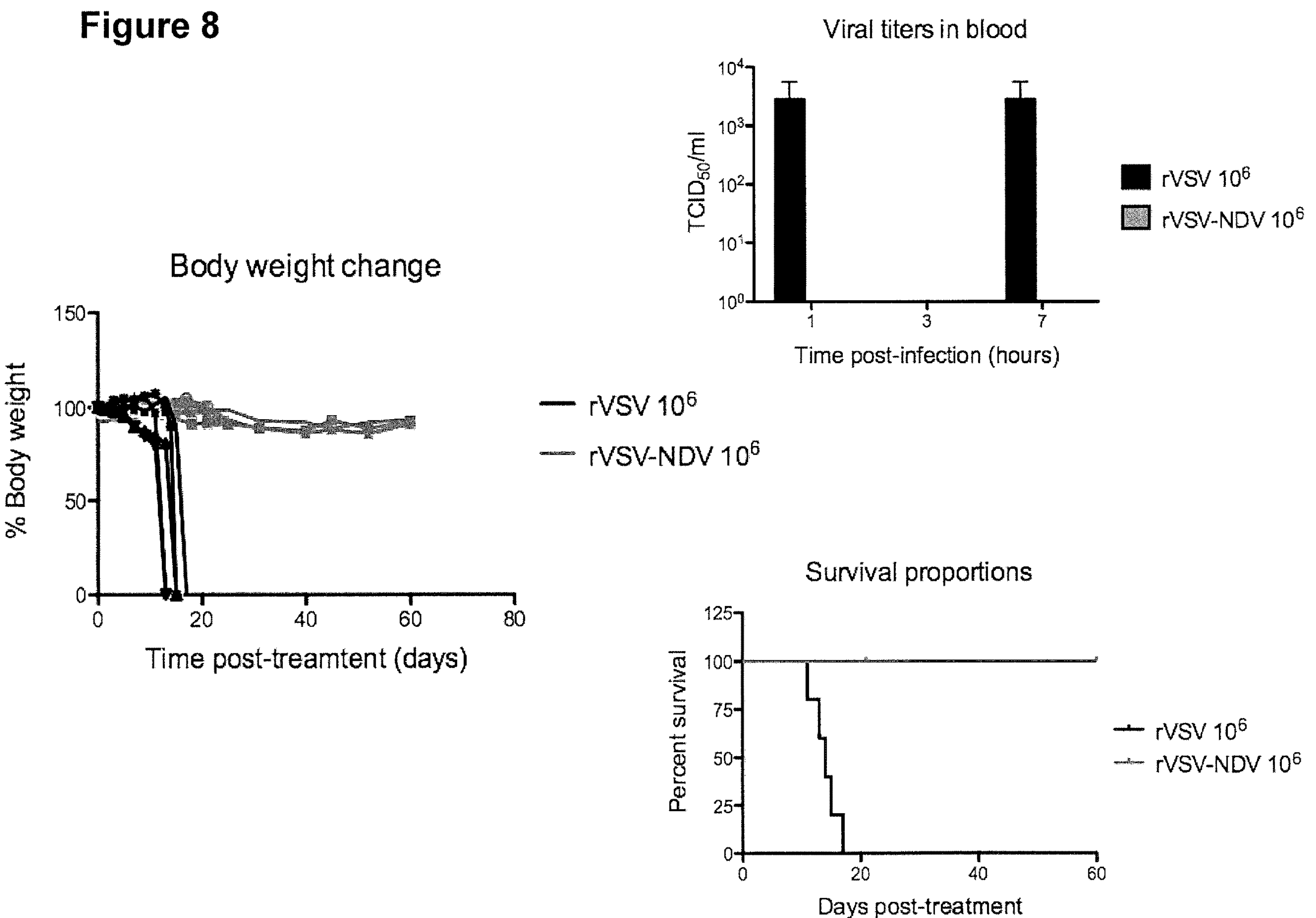

FIG. 8. Pseudotyped rVSV-NDV vector demonstrates enhanced safety compared to rVSV in immune-deficient mice.

Immune-deficient male NOD-SCID mice were treated by tail vein injection with rVSV-NDV or rVSV-GFP (referred to as rVSV in the figure for simplicity) at a dose of $10^6$ TCID50. Mice were monitored daily and euthanized at humane endpoints. Body weight changes were plotted over time with respect to the injection (left); Viral titers in blood were measured on day 1 and 7 by TCID50 analysis (center); The survival proportions were plotted by Kaplan-Maier survival curve (left).

Figure 9:
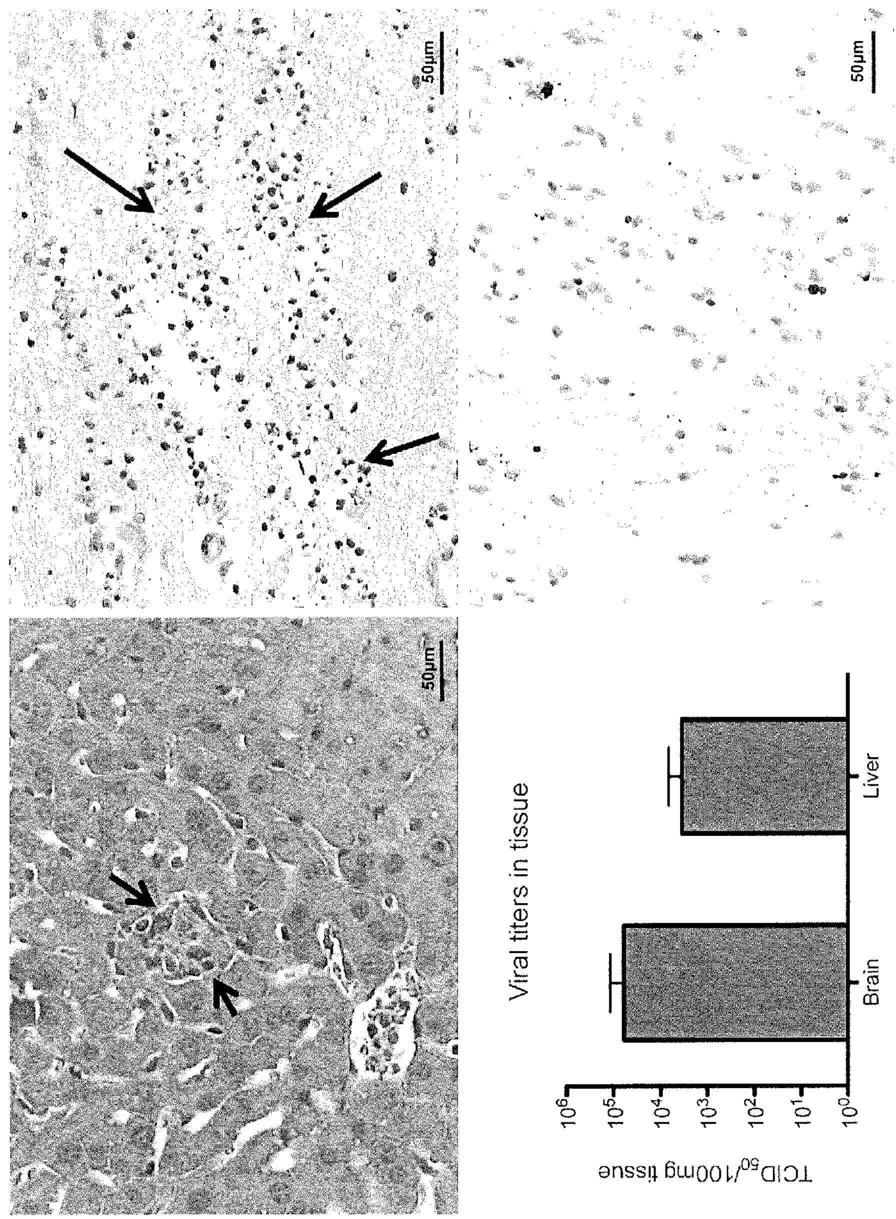

FIG. 9. Mice treated with $10^6$ TCID50 rVSV revealed pathological changes in the liver and brain.

H/E staining of liver revealed small group necrosis of hepatocytes after rVSV treatment, marked by hepatocellular degeneration with karyolysis (top left panel). Acute necrosis in the brain stem after rVSV application was observed with degenerating glial cells exhibiting pyknosis and karyorrhexis (top right panel). Degeneration of glial cells could be further confirmed by immunohistochemical staining for caspase-3 (bottom right). Representative images are shown; scale bars equal 50 μm. Viral titers were quantified from brain and liver tissue lysate from mice receiving rVSV after demonstrating signs of toxicity. Means+ SEM are shown.

EXAMPLES

1. Material and Methods 1.1 Viruses

Recombinant VSV expressing the GFP reporter (referred to herein as "rVSV") was engineered and rescued as previously described (Huang et al., 2003). Recombinant NDV harboring the F3aa(L289A) mutations and expressing the GFP reporter gene (referred to herein as "rNDV") was engineered and rescued as previously described (Altomonte et al., 2010).

Recombinant rVSV-NDV was produced by first modifying a plasmid encoding for the full-length VSV genome (pVSV-XN2) and expressing the F3aa(L289A)-modified fusion protein of NDV (Ebert et al., 2004) as an additional transcription unit between the G and L genes. The endogenous VSV glycoprotein (G) was deleted by digestion with MluI and XhoI restriction enzymes, which recognize the unique restriction sites in the 5' and 3' noncoding regions of the G, respectively. Following self-ligation of the G-deleted plasmid, a short oligonucleotide linker was inserted at the unique NheI restriction site following the NDV F gene, to create a multiple cloning site for insertion of the FIN gene. The FIN gene was amplified by PCR from a plasmid encoding the full-length NDV genome, utilizing primers to introduce PacI and PmeI restriction sites at the 5' and 3' ends of the PCR product, respectively, for insertion into the newly incorporated restriction sites in the G-deleted VSV-NDV/F3aa(L289A) plasmid. The resulting plasmid was subjected to sequence analysis to confirm the fidelity of the PCR insert, as well as the intergenic transcription start and stop sequences and the gene order. Finally, the infectious virus, referred to here as "rVSV-NDV", was rescued using the established reverse genetics system for rescuing negative-strand RNA viruses (Lawson et al., 1995).

Figure 1:
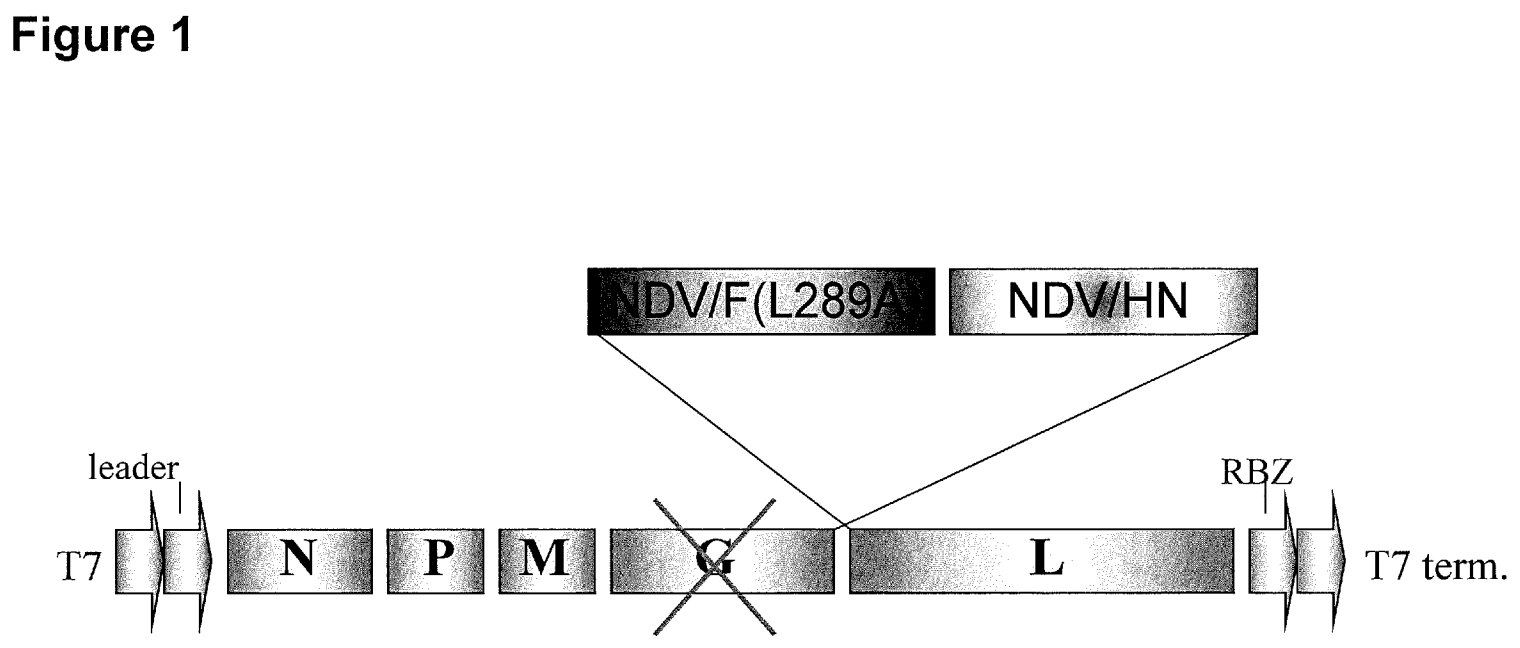

See also FIG. 1.

1.2 Cell Lines

Two human HCC cell lines (HepG2 and Huh-7) were obtained from Dr. Ulrich Lauer (University Hospital Tübingen, Germany) and maintained in Dulbecco's modified Eagle's medium (DMEM) supplemented with 10% fetal bovine serum (FBS), 1% L-glutamine (200 mM), 1% Penicillin/streptomycin, 1% non-essential amino acids and 1% sodium pyruvate. A549 cells were obtained from the ATCC (Rockville, Md.) and cultured in the same medium as the HCC cell lines. Primary human hepatocytes were derived from patients (negative for hepatitis B and C virus and human immunodeficiency virus) who had undergone surgical resection of liver tumors, in accordance with the guidelines of the charitable state-controlled Human Tissue and Cell Research (HTCR) foundation (Regensburg, Germany). The hepatocytes were maintained in HepatoZYME-SFM medium (Gibco-Invitrogen, Karlsruhe, Germany). Primary embryonic primary cortical neurons were dissociated from E16.5 mouse cortex and provided by the laboratory of Stefan Lichtenthaler (DZNE, Munich, Germany). Neuronal cultures were maintained in Neurobasal medium (Gibco) supplemented with B27 (2%), 0.5 mM glutamine, and 1% penicillin/streptomycin. All cell lines and primary cells were maintained in the 37° C. humidified incubator with 5% $CO_2$ 1.3 Microscopic Analysis The human HCC cell lines, Huh7 and HepG2, were plated at approximately 90% confluency in 6-well dishes and infected with either rVSV, rNDV, or rVSV-NDV at an MOI of 0.01 or mock-infected. Cells were visualized at 200× magnification on an Axiovert 40CFL microscope (Zeiss) at 16-, 24- and 48-hours post-infection, and representative images were captured with a Canon Powershot A620 camera attached to the microscope.

1.4 IFN Dose Response Assay

Interferon-sensitive A549 cells were plated in 24-well dishes at a density of $10^5$ cells per well and cultured overnight. The following evening they were pre-treated with different concentrations (0, 100, 500, and 1000 IU/ml) of Universal type I Interferon added directly to the culture medium. After overnight incubation, the cells were infected with either rVSV, rNDV or rVSV-NDV at a multiplicity of infection (MOI) of 0.01. 48 hours post-infection, cells were collected in 100 μl of PBS and lysed by three freeze-thaw cycles. The intratumoral virus titer was determined by $TCID_{50}$ analysis of the cell lysates.

1.5 Growth Curves (TCID50 Assay)

Viral growth curves were performed in HCC cell lines (Huh7 and HepG2), as well as in primary human hepatocytes and primary mouse neurons.

HCC cell lines were plated in 6-well dishes at a density of $3.5\times10^5$ cells per well, while PHH and neurons were seeded in collagen-coated 24-well dishes at a density of $10^5$ cells per well. Each cell line was infected with rVSV, rNDV and rVSV-NDV at a multiplicity of infection (MOI) of 0.01. The infections were performed in 1 ml of PBS (6-well dishes) or 250 μl of PBS (24-well dishes) at 37° C. for 1 hour. After incubation, cells were washed three times with PBS and fresh medium was added. Cell lysate was collected at 0, 16, 24, 48 and 72 hours post-infection for $TCID_{50}$ analysis of intracellular virus titers.

1.6 Cytotoxicity Assays (LDH or MTS Assay)

Cell viability of infected HCC cell lines (Huh7 and HepG2) and primary human hepatocytes was analyzed by measuring released Lactate Dehyrogenase (LDH) from cell culture supernatant. The cells were plated, infected and washed as in the growth curve experiments. At 24, 48 and 72 hours post-infection, aliquots of supernatant were collected, and LDH-release was quantified using the CytoTox 96 Non-Radioactive Cytotoxicity Assay protocol (Promega). For each time point, LDH-release following virus infection was calculated as a percentage of the maximum LDH-release control. Baseline LDH levels detected in the supernatant of mock-treated cells were subtracted from the values obtained from the experimental wells.

Cell viability of neurons was analyzed by MTS (3-(4,5-dimethylthiazol-2-yl)-5-(3-carbooxymethoxyphenyl)-2-(4-sulfophenyl)-2H-tetrazolium) assay using the CellTiter96 AQueous One Solution Cell Proliferation Assay (Promega, Madison, Wis.). Neurons were seeded in collagen coated 96-well dishes at a density of $5\times10^4$ cells/well and mock-treated or infected with rVSV, rNDV or rVSV-NDV at an MOI of 0.01. At 24, 48 and 72 hours post-infection, cell viability was measured according to the manufacturer's protocol. Cytotoxicity was calculated as difference in cell viability of the experimental samples compared to the uninfected controls.

1.7 Western Blots

Huh7 cells were plated in 6-well plates at approximately 90% confluence and infected with rVSV, rNDV, or rVSV-NDV at an MOI of 0.01 or mock-infected for 48 hours. The conditioned media were collected and concentrated to about 200 μl using Amicon Ultra Centrifugal filters with a 10 kD cutoff (Merck Millipore, Billerica, Mass.). Protein concentrations were quantified using the Pierce BCA Protein Assay (Thermo Fisher Scientific, Waltham, Mass.), and 10 μg of each sample was loaded onto a 7.5% denaturing SDS-PAGE gel, followed by transfer onto a nitrocellulose membrane. Protein bands were detected using specific antibodies against HMGB1 and Hsp90 (Cell Signaling Technology, Danvers, Mass.) and Hsp70 (Santa Cruz Biotechnology, Dallas, Tex.) and the appropriate secondary antibody conjugated with horseradish peroxidase. Bands were visualized using Amersham ECL Prime Western Blot Detection Reagent (GE Healthcare Life Sciences, Pittsburgh, Pa.).

2. Results

The recombinant VSV-NDV vector (FIG. 1) has been characterized in vitro for replication and cytotoxicity in tumor cells, as well as in healthy hepatocytes and neurons. We used two human hepatocellular carcinoma (HCC) cell lines as representative tumor cells, and compared the rVSV-NDV with rVSV and rNDV in terms of its relative ability to replicate and kill the cells. Although rVSV-NDV replication was a bit delayed compared to the wildtype vectors, it was able to reach similar titers at about 72 hours post-infection, which resulted in complete cell killing in vitro (FIG. 2).

In order to observe virus-induced syncytial formation, additional cells were infected with rVSV-NDV, as well as the parental rVSV and rNDV, for photomicroscopy. Microscopic analysis of the tumor cells revealed multiple foci of syncytia in the wells infected with rVSV-NDV by 16 hours post-infection, while it was significantly delayed in those infected with rNDV. As expected, cells that were treated with rVSV did not form syncytia; however, they were highly susceptible to the cytopathic effect (CPE), which is classic of VSV infection and occurred earlier than 16 hours post-infection (FIG. 3).

In order to rule out that the glycoprotein exchange inadvertently resulted in a loss of sensitivity of the vector to the antiviral actions of type I interferon (IFN), an IFN dose response was performed. The exquisite sensitivity of VSV to type I IFN is a key mechanism of tumor specificity, as tumor cells are often defective in their IFN signaling pathways, while healthy cells can efficiently clear the virus via IFN responsive genes. Although this assay revealed a relative insensitivity of rNDV to type I IFN, the rVSV-NDV vector was rapidly attenuated by the addition of IFN and reduced to levels similar to those observed for rVSV (FIG. 4).

We next performed growth curves and cytotoxicity assays in normal primary human hepatocytes and mouse neurons in order to assess the safety of rVSV-NDV. Very little replication of the pseudotyped vector could be observed over time, and titers were approximately 5 logs lower than the control VSV vector at 48 hours post-infection and 3 logs lower than rNDV at the same time-point in primary hepatocytes (FIG. 5). Although nearly all hepatocytes were dead by 72 hours post-infection with rVSV, no cytotoxicity could be observed by LDH assay in cells infected with rVSV-NDV (FIG. 5). Similarly, titers of rVSV-NDV were significantly lower than the control VSV vector in primary mouse neurons at all time-points investigated, which corresponded to similar levels of cell viability as those observed in PBS-treat neurons (FIG. 6). Taken together, rVSV-NDV showed little evidence of replication in primary healthy cells and resulted in little to no cytotoxicity in vitro, indicating that it is a substantially safer virus than both rVSV and rNDV.

To determine whether the pseudotyped rVSV vector would induce an immunogenic cell death, as has been shown for rNDV through syncytia formation, we investigated the release of high mobility group box 1 (HMGB1) and heat-shock proteins 70 and 90 from infected Huh7 cells. After a 48 hour infection, we observed relatively low levels of HMGB1, Hsp70, and Hsp90 released into the supernatant of rVSV-infected cells. However, infection with both rNDV and rVSV-NDV resulted in high levels of all three secreted markers for immunogenic cell death (FIG. 7). These results indicate that, in addition to the potent direct cytotoxicity caused by infection with the pseudotyped rVSV-NDV vector, in vivo treatment with this virus could result in substantial immune responses directed against the tumor.

In order to assess the safety of the pseudotyped rVSV-NDV vector in vivo, immune-deficient male NOD-SCID mice approximately 8 weeks of age were treated by tail vein injection with either rVSV-NDV or the control rVSV-GFP virus (N=6) at a dose of $10^6$ TCID50 per mouse. Mice were monitored daily for body weight and overall physical appearance, and they were euthanized at humane endpoints. Blood was sampled on day 1, 3, 7, 14, and at the time of euthanization for analysis serum chemistry and circulating virus titers. Two mice receiving rVSV-GFP rapidly began losing weight during the first week after treatment, and all six died acutely or were euthanized due to extreme body weight loss, dehydration, signs of distress (changes in posture, impaired movement, isolation, etc.), and/or signs of neurotoxicity (limb paralysis and circling) between 11 and 17 days post-treatment (FIG. 8). Additionally, infectious virus titers could be recovered from the blood on day 1 and 7 post-treatment (FIG. 8, center). In contrast, the mice who received rVSV-NDV lost only negligible amounts of weight, appeared healthy and exhibited normal behavior throughout the study. Three of these mice were euthanized at 21 days post-treatment for histological analysis of major organs, while the remaining animals were monitored for 60 days post-treatment, at which time they were euthanized for pathological analysis. No infectious virus titers could be detected in the blood of mice treated with rVSV-NDV at any time-point analyzed. Plasma measurements of liver function (GPT) and kidney function (BUN and Creatinine) revealed no abnormal values for either treatment group (data not shown).

Tissue sections were examined by a pathologist who was blinded to the treatment groups of the specimens. Histological analysis revealed no major pathological findings in tissue excised from mice treated with rVSV-NDV, either euthanized on day 21 or day 60. Furthermore, no detectable titers within the brain or liver tissue could be observed in mice treated with rVSV-NDV (data not shown). In stark contrast, mice that received rVSV-GFP at the same dose exhibited heavy intrasinusoidal edema, moderate acute hepatitis with single cell and small group necrosis, and apoptosis of hepatic tissue (FIG. 9). Furthermore, acute necrosis in the brain stem, with degenerating glial cells exhibiting pyknosis and karyorhexis could be observed. Degeneration of glial cells was further confirmed by immunohistochemical staining for caspase-3. TCID50 analysis of tissue lysates revealed quantifiable levels of infectious VSV in the liver and brain at the time of necropsy.

The features disclosed in the foregoing description, in the claims and/or in the accompanying drawings may, both separately and in any combination thereof, be material for realizing the invention in diverse forms thereof.

REFERENCES

Altomonte, J., L. Wu, et al. (2008). "Exponential enhancement of oncolytic vesicular stomatitis virus potency by vector-mediated suppression of inflammatory responses in vivo." *Mol Ther* 16(1): 146-153.

Altomonte, J., S. Marozin, et al. (2010). "Engineered newcastle disease virus as an improved oncolytic agent against hepatocellular carcinoma." *Mol Ther* 18(2): 275-284.

Ayala-Breton, C., G. N. Barber, et al. (2012). "Retargeting vesicular stomatitis virus using measles virus envelope glycoproteins." *Hum Gene Ther* 23(5): 484-491.

Bull, C., M. A. Stoel, et al. (2014). "Sialic acids sweeten a tumor's life." *Cancer Res* 74(12): 3199-3204.

Coffey, M. C., Strong, J. E., Forsyth, P. A., Lee, P. W. (1998). "Reovirus therapy of tumors with activated Ras pathway." *Science* 282: 1332-1334.

Cuadrado-Castano, S., M. T. Sanchez-Aparicio, et al. (2015). "The therapeutic effect of death: Newcastle disease virus and its antitumor potential." *Virus Res* 209: 56-66.

Ebert, O., K. Shinozaki, et al. (2004). "Syncytia induction enhances the oncolytic potential of vesicular stomatitis virus in virotherapy for cancer." *Cancer Res* 64(9): 3265-70.

Ebert, O., S. Harbaran, et al. (2005). "Systemic therapy of experimental breast cancer metastases by mutant vesicular stomatitis virus in immune-competent mice." *Cancer Gene Ther* 12(4): 350-358.

Edge, R. E., T. J. Falls, et al. (2008). "A let-7 MicroRNA-sensitive vesicular stomatitis virus demonstrates tumor-specific replication." *Mol Ther* 16(8): 1437-1443.

Everts, B. and H. G. van der Poel (2005). "Replication-selective oncolytic viruses in the treatment of cancer." *Cancer Gene Ther* 12(2): 141-161.

Huang H. G., O. Ebert, et al. (2003). "Oncolysis of hepatic metastasis of colorectal cancer by recombinant vesicular stomatitis virus in immune competent mice." *Mol Ther* 8(3): 434-40.

Johnson, J. E., F. Nasar, et al. (2007). "Neurovirulence properties of recombinant vesicular stomatitis virus vectors in non-human primates." *Virology* 360(1): 36-49.

Kelly, E. J., R. Nace, et al. (2010). "Attenuation of vesicular stomatitis virus encephalitis through microRNA targeting." *J Virol* 84(3): 1550-1562.

Kim, D., Martuza, R. L., and Zwiebel, J. (2001). "Replication-selective virotherapy for cancer: biological principles, risk management, and future directions." *Nat Med* 7: 781-787.

Lawson, N. D., E. A. Stillman, et al. (1995). "Recombinant vesicular stomatitis viruses from DNA." *Proc Natl Acad Sci* 92: 4477-81.

Liu, Y. P., S. P. Russell, et al. (2014). "Ablation of nectin4 binding compromises CD46 usage by a hybrid vesicular stomatitis virus/measles virus." *J Virol* 88(4): 2195-2204.

Lorence, R. M., Katubig, B. B., Reichard, K. W., et al (1994). "Complete regression of human fibrosarcoma xenografts after local Newcastle disease virus therapy." *Cancer Research* 54: 6017-6021.

Muik, A., I. Kneiske, et al. (2011). "Pseudotyping vesicular stomatitis virus with lymphocytic choriomeningitis virus glycoproteins enhances infectivity for glioma cells and minimizes neurotropism." *J Virol* 85(11): 5679-5684.

Patel, M. R. and R. A. Kratzke (2013). "Oncolytic virus therapy for cancer: the first wave of translational clinical trials." *Transl Res* 161(4): 355-364.

Park, M. S., Steel, J., Garcia-Sastre, A., et al (2006). "Engineered viral vaccine constructs with dual specificity: Avian influenza and Newcastle disease." PNAS 103 (21): 8203-8.

Peeters, B. P., O. S. de Leeuw, et al. (1999). "Rescue of Newcastle disease virus from cloned cDNA: evidence that cleavability of the fusion protein is a major determinent of virulence." *J Virol* 73(6):5001-9.

Peng, K. W., Ahmann, G. J., Pham, L, et al (2001). "Systemic therapy of myeloma xenografts by an attenuated measles virus." *Blood* 98: 2002-2007.

Quiroz, E., N. Moreno, et al. (1988). "A human case of encephalitis associated with vesicular stomatitis virus (Indiana serotype) infection." *Am J Trop Med Hyg* 39(3): 312-314.

Stojdl, D. F., Lichty, tenOever, B. R., et al (2003). "VSV strains with defects in their ability to shutdown innate immunity are potent systemic anti-cancer agents." *Cancer Cell* 4(4): 263-275.

van den Pol, A., Dalton, K., and Rose, J. (2002). "Relative neurotropism of a recombinant rhabdovirus expressing a green fluorescent envelope glycoprotein." *Journal of Virology* 76(3): 1309-1327.

Vigil, A., M. S. Park, et al. (2007). "Use of reverse genetics to enhance the oncolytic properties of Newcastle disease virus." *Cancer Res* 67(17): 8285-8292.

The invention claimed is:

1. A recombinant oncolytic virus, comprising a vesicular stomatitis virus (VSV), wherein glycoprotein (G protein) of VSV is deleted, and which comprises a modified fusion protein (F protein) of Newcastle disease virus (NDV), and the hemagglutinin neuraminidase (I-IN) protein of NDV.

2. The recombinant oncolytic virus of claim 1, wherein the modified fusion protein (F protein) of NDV is a F3aa-modified F protein, and/or wherein the modified fusion protein comprises at least one amino acid substitution in the protease cleavage site, and/or wherein the G protein of VSV is replaced by the modified fusion protein and the HN protein of NDV.

3. The recombinant oncolytic virus of claim 1, wherein the modified fusion protein (F protein) of NDV comprises the amino acid sequence of SEQ ID NO: 10 or SEQ ID NO: 12, and/or wherein the modified fusion protein (F protein) of NDV is encoded by a nucleotide sequence of SEQ ID NO: 9 or SEQ ID NO: 11, and/or wherein the HN protein of NDV comprises the amino acid sequence of SEQ ID NO: 6, and/or wherein the HN protein of NDV is encoded by a nucleotide sequence of SEQ ID NO: 5.

4. A nucleic acid encoding a recombinant oncolytic virus according to claim 1.

5. A vector comprising a nucleic acid of claim 4.

6. The nucleic acid of claim 4, comprising the nucleotide sequence of SEQ ID NO: 13, and/or comprising a nucleotide sequence coding for an amino acid sequence having SEQ ID NOs: 6, 12, and 14 to 17.

7. A pharmaceutical composition, comprising:

(i) the recombinant oncolytic virus of claim 1 or a nucleic acid encoding a recombinant oncolytic virus according to claim 1; and (ii) pharmaceutically acceptable carrier(s) and/or excipient(s).

8. The pharmaceutical composition of claim 7, further comprising one or more compounds selected from chemotherapeutic agents, radiotherapeutic agents, tumor vaccines, immune checkpoint inhibitors, cell carrier systems, small molecule inhibitors,
embolization agents, and
shielding polymers.

9. The pharmaceutical composition of claim 7, formulated for delivery via, route selected from intravenous, intraarterial, intradermal, subcutaneous, intramuscular, intratumoral, intraosseous, intraperitoneal, intrathecal, epidural, intracardiac, intraarticular, intracavernous, intracerebral, intracerebroventricular and intravitreal.

10. A method for oncolytic therapy wherein said method comprises the step of administering a therapeutically effective amount of the recombinant oncolytic virus according to claim 1 or a nucleic acid encoding the recombinant oncolytic virus according to claim 1, to a patient.

11. The method according to claim 10, further comprising the step of administering one or more additional agents selected from cell carrier systems,
immunotherapies,
and
standard tumor therapies,
to said patient.

12. A method of treatment of cancer comprising the step of administering to a subject in need thereof a therapeutically effective amount of the recombinant oncolytic virus of claim 1 or a nucleic acid encoding the recombinant oncolytic virus according to claim 1.

13. The method according to claim 11, wherein the cell carrier system is selected from T cells, dendritic cells, NK cells, and mesenchymal stem cells; the immunotherapy is selected from tumor vaccines and immune checkpoint inhibitors; and the standard tumor therapy is selected from radiofrequency ablation, chemotherapy, embolization, and small molecule inhibitors.

14. The vector according to claim 5, further comprising one or more reporter genes and/or genes to be delivered to a target cell or tissue.

15. The vector according to claim 14, wherein the reporter gene is selected from HSV1-sr39TK, the sodium iodide symporter (NIS), somatostatin receptor 2 (SSTR2), luciferase, green fluorescence protein (GFP), lacZ, and tyrosinase; and the gene to be delivered to a target cell or tissue is selected from immune stimulating genes, immune checkpoint inhibitory antibodies, and tumor associated antigens (TAA).

16. The recombinant oncolytic virus of claim 1, wherein the modified fusion protein (F protein) of NDV comprises an amino acid substitution at position L289.

17. The recombinant oncolytic virus of claim 16, wherein the amino acid substitution is L289A.

18. The vector according to claim 5, comprising the nucleotide sequence of SEQ ID NO: 13, and/or comprising a nucleotide sequence coding for an amino sequence having SEQ ID NOs: 6, 12, and 14 to 17.

* * * * *

UNITED STATES PATENT AND TRADEMARK OFFICE

CERTIFICATE OF CORRECTION

PATENT NO. : 10,906,942 B2
APPLICATION NO. : 16/097748
DATED : February 2, 2021
INVENTOR(S) : Oliver Ebert and Jennifer Altomonte It is certified that error appears in the above-identified patent and that said Letters Patent is hereby corrected as shown below:

In the Specification

Column 1,
Line 37 "Kim et al., 2001" should read --Kirn et al., 2001--.
Line 64 "(Kim et al., 2001)" should read --(Kirn et al., 2001)--.

Column 2,
Line 41 "(Stoj dl et al., 2003)" should read --(Stojdl et al., 2003)--.

Column 6,
Line 47 "TNEAVREVTD" should read --TNEAVHEVTD--.

Column 7,
Line 7 "TCGOTAG" should read --TCGGTAG--.

Column 10,
Line 22 "FIN protein" should read --HN protein--.
Line 23 "SEQ ID NO, 5" should read --SEQ ID NO. 5--.
Line 48 "or B7-1-13;" should read --or B7-H3--.

Column 11,
Line 43 "phaimaceutical" should read --pharmaceutical--.

Column 13,
Line 41 "of the FIN" should read --of the HN--.

Column 16,
Lines 40-41 "the FIN gene. The FIN gene" should read --the HN gene. The HN gene--.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

Column 20,
Line 56 "Kim, D.," should read --Kirn, D.,--.

In the Claims

Column 93,
Line 50 Claim 1, "(I-IN) protein" should read --(HN) protein--.

SEQUENCE LISTING

```
<160> NUMBER OF SEQ ID NOS: 17

<210> SEQ ID NO 1
<211> LENGTH: 11161
<212> TYPE: DNA
<213> ORGANISM: Vesicular stomatitis virus

<400> SEQUENCE: 1

acgaagacaa acaaaccatt attatcatta aaaggctcag gagaaacttt aacagtaatc     60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact tgtatggagc attaaaggac    300
atccggggta agttggataa agattggtca agtttcggaa taaacatcgg gaaagcaggg    360
gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600
gacatttttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca acatttggac acctctgcaa aataaccgga    780
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata acaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gaccctataa ttctcagatc acctattata tattatgcta catatgaaaa   1380
```

-continued

```
aaactaacag atatcatgga taatctcaca aaagttcgtg agtatctcaa gtcctattct   1440

cgtctggatc aggcggtagg agagatagat gagatcgaag cacaacgagc tgaaaagtcc   1500

aattatgagt tgttccaaga ggatggagtg gaagagcata ctaagccctc ttattttcag   1560

gcagcagatg attctgacac agaatctgaa ccagaaattg aagacaatca aggtttgtat   1620

gcacaggatc cagaagctga gcaagttgaa ggctttatac aggggccttt agatgactat   1680

gcagatgagg aagtggatgt tgtatttact tcggactgga aaccacctga gcttgaatct   1740

gacgagcatg gaaagacctt acggttgaca tcgccagagg gtttaagtgg agagcagaaa   1800

tcccagtggc tttcgacgat taaagcagtc gtgcaaagtg ccaaatactg gaatctggca   1860

gagtgcacat ttgaagcatc gggagaaggg gtcattatga aggagcgcca gataactccg   1920

gatgtatata aggtcactcc agtgatgaac acacatccgt cccaatcaga agcagtatca   1980

gatgtttggt ctctctcaaa gacatccatg actttccaac ccaagaaagc aagtcttcag   2040

cctctcacca tatccttgga tgaattgttc tcatctagag gagagttcat ctctgtcgga   2100

ggtgacggac gaatgtctca taaagaggcc atcctgctcg gcctgagata caaaaagttg   2160

tacaatcagg cgagagtcaa atattctctg tagactatga aaaaaagtaa cagatatcac   2220

gatctaagtg ttatcccaat ccattcatca tgagttcctt aaagaagatt ctcggtctga   2280

aggggaaagg taagaaatct aagaaattag ggatcgcacc acccccttat gaagaggaca   2340

ctagcatgga gtatgctccg agcgctccaa ttgacaaatc ctattttgga gttgacgaga   2400

tggacaccta tgatccgaat caattaagat atgagaaatt cttctttaca gtgaaaatga   2460

cggttagatc taatcgtccg ttcagaacat actcagatgt ggcagccgct gtatcccatt   2520

gggatcacat gtacatcgga atggcaggga aacgtccctt ctacaaaatc ttggcttttt   2580

tgggttcttc taatctaaag gccactccag cggtattggc agatcaaggt caaccagagt   2640

atcacactca ctgcgaaggc agggcttatt tgccacatag gatggggaag acccctccca   2700

tgctcaatgt accagagcac ttcagaagac cattcaatat aggtctttac aagggaacga   2760

ttgagctcac aatgaccatc tacgatgatg agtcactgga agcagctcct atgatctggg   2820

atcatttcaa ttcttccaaa ttttctgatt tcagagagaa ggccttaatg tttggcctga   2880

ttgtcgagaa aaaggcatct ggagcgtggg tcctggattc tatcagccac ttcaaatgag   2940

ctagtctaac ttctagcttc tgaacaatcc ccggtttact cagtctctcc taattccagc   3000

ctctcgaaca actaatatcc tgtcttttct atccctatga aaaaaactaa cagagatcga   3060

tctgtttcct tgacactatg aagtgccttt tgtacttagc ctttttattc attggggtga   3120

attgcaagtt caccatagtt tttccacaca accaaaaagg aaactggaaa aatgttcctt   3180

ctaattacca ttattgcccg tcaagctcag atttaaattg gcataatgac ttaataggca   3240

cagccataca agtcaaaatg cccaagagtc acaaggctat tcaagcagac ggttggatgt   3300

gtcatgcttc caaatgggtc actacttgtg atttccgctg gtatggaccg aagtatataa   3360

cacagtccat ccgatccttc actccatctg tagaacaatg caaggaaagc attgaacaaa   3420

cgaaacaagg aacttggctg aatccaggct tccctcctca aagttgtgga tatgcaactg   3480

tgacggatgc cgaagcagtg attgtccagg tgactcctca ccatgtgctg gttgatgaat   3540

acacaggaga atgggttgat tcacagttca tcaacggaaa atgcagcaat tacatatgcc   3600

ccactgtcca taactctaca acctggcatt ctgactataa ggtcaaaggg ctatgtgatt   3660

ctaacctcat ttccatggac atcaccttct tctcagagga cggagagcta tcatccctgg   3720

gaaaggaggg cacagggttc agaagtaact actttgctta tgaaactgga ggcaaggcct   3780
```

-continued

```
gcaaaatgca atactgcaag cattggggag tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg gacccaatgg agttctgagg accagttcag   4260
gatataagtt tcctttatac atgattggac atggtatgtt ggactccgat cttcatctta   4320
gctcaaaggc tcaggtgttc gaacatcctc acattcaaga cgctgcttcg caacttcctg   4380
atgatgagag tttatttttt ggtgatactg ggctatccaa aaatccaatc gagcttgtag   4440
aaggttggtt cagtagttgg aaaagctcta ttgcctcttt tttctttatc atagggttaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgcacaac agattcttca tgtttggacc aaatcaactt gtgataccat gctcaaagag   4680
gcctcaatta tatttgagtt tttaattttt atgaaaaaaa ctaacagcaa tcatggaagt   4740
ccacgatttt gagaccgacg agttcaatga tttcaatgaa gatgactatg ccacaagaga   4800
attcctgaat cccgatgagc gcatgacgta cttgaatcat gctgattaca atttgaattc   4860
tcctctaatt agtgatgata ttgacaattt gatcaggaaa ttcaattctc ttccgattcc   4920
ctcgatgtgg gatagtaaga actgggatgg agttcttgag atgttaacat catgtcaagc   4980
caatcccatc tcaacatctc agatgcataa atggatggga agttggttaa tgtctgataa   5040
tcatgatgcc agtcaagggt atagtttttt acatgaagtg gacaaagagg cagaaataac   5100
atttgacgtg gtggagacct tcatccgcgg ctggggcaac aaaccaattg aatacatcaa   5160
aaaggaaaga tggactgact cattcaaaat tctcgcttat ttgtgtcaaa agtttttgga   5220
cttacacaag ttgacattaa tcttaaatgc tgtctctgag gtggaattgc tcaacttggc   5280
gaggactttc aaaggcaaag tcagaagaag ttctcatgga acgaacatat gcaggattag   5340
ggttcccagc ttgggtccta cttttatttc agaaggatgg gcttacttca agaaacttga   5400
tattctaatg gaccgaaact ttctgttaat ggtcaaagat gtgattatag ggaggatgca   5460
aacggtgcta tccatggtat gtagaataga caacctgttc tcagagcaag acatcttctc   5520
ccttctaaat atctacagaa ttggagataa aattgtggag aggcagggaa atttttctta   5580
tgacttgatt aaaatggtgg aaccgatatg caacttgaag ctgatgaaat tagcaagaga   5640
atcaaggcct ttagtcccac aattccctca ttttgaaaat catatcaaga cttctgttga   5700
tgaaggggca aaaattgacc gaggtataag attcctccat gatcagataa tgagtgtgaa   5760
aacagtggat ctcacactgg tgatttatgg atcgttcaga cattggggtc atccttttat   5820
agattattac actggactag aaaaattaca ttcccaagta accatgaaga aagatattga   5880
tgtgtcatat gcaaaagcac ttgcaagtga tttagctcgg attgttctat ttcaacagtt   5940
caatgatcat aaaaagtggt tcgtgaatgg agacttgctc cctcatgatc atccctttaa   6000
aagtcatgtt aaagaaaata catggcccac agctgctcaa gttcaagatt ttggagataa   6060
atggcatgaa cttccgctga ttaaatgttt tgaaataccc gacttactag acccatcgat   6120
```

-continued

```
aatatactct gacaaaagtc attcaatgaa taggtcagag gtgttgaaac atgtccgaat   6180

gaatccgaac actcctatcc ctagtaaaaa ggtgttgcag actatgttgg acacaaaggc   6240

taccaattgg aaagaatttc ttaaagagat tgatgagaag ggcttagatg atgatgatct   6300

aattattggt cttaaaggaa aggagaggga actgaagttg gcaggtagat tttctccct    6360

aatgtcttgg aaattgcgag aatactttgt aattaccgaa tatttgataa agactcattt   6420

cgtccctatg tttaaaggcc tgacaatggc ggacgatcta actgcagtca ttaaaaagat   6480

gttagattcc tcatccggcc aaggattgaa gtcatatgag gcaatttgca tagccaatca   6540

cattgattac gaaaaatgga ataaccacca aaggaagtta tcaaacggcc cagtgttccg   6600

agttatgggc cagttcttag gttatccatc cttaatcgag agaactcatg aatttttga    6660

gaaaagtctt atatactaca atggaagacc agacttgatg cgtgttcaca acaacacact   6720

gatcaattca acctcccaac gagtttgttg gcaaggacaa gagggtggac tggaaggtct   6780

acggcaaaaa ggatggacta tcctcaatct actggttatt caaagagagg ctaaaatcag   6840

aaacactgct gtcaaagtct tggcacaagg tgataatcaa gttatttgca cacagtataa   6900

aacgaagaaa tcgagaaacg ttgtagaatt acagggtgct ctcaatcaaa tggtttctaa   6960

taatgagaaa attatgactg caatcaaaat agggacaggg aagttaggac ttttgataaa   7020

tgacgatgag actatgcaat ctgcagatta cttgaattat ggaaaaatac cgattttccg   7080

tggagtgatt agagggttag agaccaagag atggtcacga gtgacttgtg tcaccaatga   7140

ccaaataccc acttgtgcta atataatgag ctcagtttcc acaaatgctc tcaccgtagc   7200

tcattttgct gagaacccaa tcaatgccat gatacagtac aattattttg ggacatttgc   7260

tagactcttg ttgatgatgc atgatcctgc tcttcgtcaa tcattgtatg aagttcaaga   7320

taagataccg ggcttgcaca gttctacttt caaatacgcc atgttgtatt tggacccttc   7380

cattggagga gtgtcgggca tgtctttgtc caggtttttg attagagcct tcccagatcc   7440

cgtaacagaa agtctctcat tctggagatt catccatgta catgctcgaa gtgagcatct   7500

gaaggagatg agtgcagtat ttggaaaccc cgagatagcc aagtttcgaa taactcacat   7560

agacaagcta gtagaagatc caacctctct gaacatcgct atgggaatga gtccagcgaa   7620

cttgttaaag actgaggtta aaaaatgctt aatcgaatca agacaaacca tcaggaacca   7680

ggtgattaag gatgcaacca tatatttgta tcatgaagag gatcggctca gaagtttctt   7740

atggtcaata aatcctctgt tccctagatt tttaagtgaa ttcaaatcag gcactttttt   7800

gggagtcgca gacgggctca tcagtctatt tcaaaattct cgtactattc ggaactcctt   7860

taagaaaaag tatcataggg aattggatga tttgattgtg aggagtgagg tatcctcttt   7920

gacacattta gggaaacttc atttgagaag ggggatcatgt aaaatgtgga catgttcagc  7980

tactcatgct gacacattaa gatacaaatc ctggggccgt acagttattg ggacaactgt   8040

accccatcca ttagaaatgt tgggtccaca acatcgaaaa gagactcctt gtgcaccatg   8100

taacacatca gggttcaatt atgtttctgt gcattgtcca gacgggatcc atgacgtctt   8160

tagttcacgg ggaccattgc ctgcttatct agggtctaaa acatctgaat ctacatctat   8220

tttgcagcct tgggaaaggg aaagcaaagt cccactgatt aaaagagcta cacgtcttag   8280

agatgctatc tcttggtttg ttgaacccga ctctaaacta gcaatgacta tactttctaa   8340

catccactct ttaacaggcg aagaatggac caaaaggcag catgggttca aaagaacagg   8400

gtctgccctt cataggtttt cgacatctcg gatgagccat ggtgggttcg catctcagag   8460

cactgcagca ttgaccaggt tgatggcaac tacagacacc atgagggatc tgggagatca   8520
```

```
gaatttcgac tttttattcc aagcaacgtt gctctatgct caaattacca ccactgttgc   8580
aagagacgga tggatcacca gttgtacaga tcattatcat attgcctgta agtcctgttt   8640
gagacccata gaagagatca ccctggactc aagtatggac tacacgcccc cagatgtatc   8700
ccatgtgctg aagacatgga ggaatgggga aggttcgtgg ggacaagaga taaaacagat   8760
ctatccttta gaagggaatt ggaagaattt agcacctgct gagcaatcct atcaagtcgg   8820
cagatgtata ggttttctat atggagactt ggcgtataga aaatctactc atgccgagga   8880
cagttctcta tttcctctat ctatacaagg tcgtattaga ggtcgaggtt tcttaaaagg   8940
gttgctagac ggattaatga gagcaagttg ctgccaagta atacaccgga gaagtctggc   9000
tcatttgaag aggccggcca acgcagtgta cggaggtttg atttacttga ttgataaatt   9060
gagtgtatca cctccattcc tttctcttac tagatcagga cctattagag acgaattaga   9120
aacgattccc cacaagatcc caacctccta tccgacaagc aaccgtgata tgggggtgat   9180
tgtcagaaat tacttcaaat accaatgccg tctaattgaa aagggaaaat acagatcaca   9240
ttattcacaa ttatggttat tctcagatgt cttatccata gacttcattg gaccattctc   9300
tatttccacc accctcttgc aaatcctata caagccattt ttatctggga aagataagaa   9360
tgagttgaga gagctggcaa atctttcttc attgctaaga tcaggagagg ggtgggaaga   9420
catacatgtg aaattcttca ccaaggacat attattgtgt ccagaggaaa tcagacatgc   9480
ttgcaagttc gggattgcta aggataataa taaagacatg agctatcccc cttggggaag   9540
ggaatccaga gggacaatta caacaatccc tgtttattat acgaccaccc cttacccaaa   9600
gatgctagag atgcctccaa gaatccaaaa tcccctgctg tccggaatca ggttgggcca   9660
attaccaact ggcgctcatt ataaaattcg gagtatatta catggaatgg gaatccatta   9720
cagggacttc ttgagttgtg gagacggctc cggagggatg actgctgcat tactacgaga   9780
aaatgtgcat agcagaggaa tattcaatag tctgttagaa ttatcagggt cagtcatgcg   9840
aggcgcctct cctgagcccc ccagtgccct agaaacttta ggaggagata aatcgagatg   9900
tgtaaatggt gaaacatgtt gggaatatcc atctgactta tgtgacccaa ggacttggga   9960
ctatttcctc cgactcaaag caggcttggg gcttcaaatt gatttaattg taatggatat  10020
ggaagttcgg gattcttcta ctagcctgaa aattgagacg aatgttagaa attatgtgca  10080
ccggattttg gatgagcaag gagttttaat ctacaagact tatggaacat atatttgtga  10140
gagcgaaaag aatgcagtaa caatccttgg tcccatgttc aagacggtcg acttagttca  10200
aacagaattt agtagttctc aaacgtctga agtatatatg gtatgtaaag gtttgaagaa  10260
attaatcgat gaacccaatc ccgattggtc ttccatcaat gaatcctgga aaaacctgta  10320
cgcattccag tcatcagaac aggaatttgc cagagcaaag aaggttagta catactttac  10380
cttgacaggt attccctccc aattcattcc tgatcctttt gtaaacattg agactatgct  10440
acaaatattc ggagtaccca cgggtgtgtc tcatgcggct gccttaaaat catctgatag  10500
acctgcagat ttattgacca ttagcctttt ttatatggcg attatatcgt attataacat  10560
caatcatatc agagtaggac cgatacctcc gaacccccca tcagatggaa ttgcacaaaa  10620
tgtggggatc gctataactg gtataagctt ttggctgagt ttgatggaga aagacattcc  10680
actatatcaa cagtgtttag cagttatcca gcaatcattc ccgattaggt gggaggctgt  10740
ttcagtaaaa ggaggataca agcagaagtg gagtactaga ggtgatgggc tcccaaaaga  10800
tacccgaact tcagactcct tggccccaat cgggaactgg atcagatctc tggaattggt  10860
```

```
ccgaaaccaa gttcgtctaa atccattcaa tgagatcttg ttcaatcagc tatgtcgtac  10920

agtggataat catttgaaat ggtcaaattt gcgaagaaac acaggaatga ttgaatggat  10980

caatagacga atttcaaaag aagaccggtc tatactgatg ttgaagagtg acctacacga  11040

ggaaaactct tggagagatt aaaaaatcat gaggagactc caaactttaa gtatgaaaaa  11100

aactttgatc cttaagaccc tcttgtggtt tttatttttt atctggtttt gtggtcttcg  11160

t                                                                  11161
```

<210> SEQ ID NO 2
<211> LENGTH: 1665
<212> TYPE: DNA
<213> ORGANISM: Vesicular stomatitis virus

<400> SEQUENCE: 2

```
aacagagatc gatctgtttc cttgacacca tgaagtgctt tttgtactta gcttttttat     60

tcatcggggt gaattgcaag ttcaccatag tttttccaca caaccaaaaa ggaaactgga    120

aaaatgttcc ttccaattac cattattgcc cgtcaagctc agatttaaat tggcataatg    180

acttaatagg cacaggctta caagtcaaaa tgcccaagag tcacaaggct attcaagcag    240

acggttggat gtgtcatgct tccaaatggg tcactacttg tgatttccgc tggtacggac    300

cgaagtatat aacacattcc atccgatcct tcactccatc tgtagaacaa tgcaaggaaa    360

gcattgaaca aacgaaacaa ggaacttggc tgaatccagg cttccctcct caaagttgtg    420

gatatgcaac tgtgacggat gccgaagcag tgattgtcca ggtgactcct caccatgtgc    480

ttgttgatga atacacagga gaatgggttg attcacagtt catcaacgga aaatgcagca    540

atgacatatg ccccactgtc cataactcca caacctggca ttccgactat aaggtcaaag    600

ggctatgtga ttctaacctc atttccacgg acatcacctt cttctcagag gacagagagc    660

tatcatccct aggaaaggag ggcacagggt tcagaagtaa ctactttgct tatgaaactg    720

gagacaaggc ctgcaaaatg cagtactgca agcattgggg agtcagactc ccatcaggtg    780

tctggttcga gatggctgat aaggatctct ttgctgcagc cagattccct gaatgcccag    840

aagggtcaag tatctctgct ccatctcaga cctcagtgga tgtaagtctc attcaggacg    900

ttgagaggat cttggattat tccctctgcc aagaaacctg gagcaaaatc agagcgggtc    960

ttcccatctc tccagtggat ctcagctatc ttgctcctaa aaacccagga accggtcctg   1020

cctttaccat aatcaatggt accctaaaat actttgagac cagatacatc agagtcgata   1080

ttgctgctcc aatcctctca agaatggtcg gaatgatcag tggaactacc acagaaaggg   1140

aactgtggga tgactgggct ccatatgaag acgtggaaat tggacccaat ggagttctga   1200

ggaccagttc aggatataag tttcctttat atatgattgg acatggtatg ttggactccg   1260

gtcttcatct tagctcaaag gctcaggtgt ttgaacatcc tcacattcaa gacgctgctt   1320

cgcagcttcc tgatgatgag attttatttt ttggtgatac tgggctatcc aaaaatccaa   1380

tcgactttgt cgaaggttgg ttcagtagtt ggaagagctc cattgcctct tttttcttta   1440

tcatagggtt aatcattgga ctattcttgg ttctccgagt tggtatttat ctttacatta   1500

aattaaagca caccaagaaa agacagattt atacagacat agagatgaac cgacttggaa   1560

ggtaactcaa atcctgcaca acagattctt catgtttgga ccaaatcaac ttgtgatacc   1620

atgctcaaag aggcctcaat tatatttgag tttttaattt ttatg                   1665
```

<210> SEQ ID NO 3
<211> LENGTH: 511

```
<212> TYPE: PRT
<213> ORGANISM: Vesicular stomatitis virus

<400> SEQUENCE: 3

Met Lys Cys Phe Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Gly Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
        195                 200                 205

Arg Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400
```

```
Tyr Met Ile Gly His Gly Met Leu Asp Ser Gly Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ile Leu Phe Phe Gly Asp Thr Gly Leu Ser Lys
        435                 440                 445

Asn Pro Ile Asp Phe Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Tyr Ile Lys Leu Lys His Thr Lys
                485                 490                 495

Lys Arg Gln Ile Tyr Thr Asp Ile Glu Met Asn Arg Leu Gly Arg
            500                 505                 510


<210> SEQ ID NO 4
<211> LENGTH: 15186
<212> TYPE: DNA
<213> ORGANISM: Newcastle disease virus

<400> SEQUENCE: 4

accaaacaga gaatccgtaa gttacgataa aaggcgaagg agcaattgaa gtcgcacggg     60

tagaaggtgt gaatctcgag tgcgagcccg aagcacaaac tcgaggaagc cttctgccaa    120

catgtcttcc gtattcgacg agtacgaaca gctcctcgcg gctcagactc gccccaatgg    180

agctcatgga ggggggagaa aagggagtac cttaaaagta gacgtcccgg tattcactct    240

taacagtgat gacccagaag ataggtggag ctttgtggta ttctgcctcc ggattgctgt    300

tagcgaagat gccaacaaac cactcaggca aggtgctctc atatctcttt tatgctccca    360

ctcacaggta atgaggaacc atgttgccct tgcagggaaa cagaatgaag ccacattggc    420

cgtgcttgag attgatggct ttgccaacgg cacgccccag ttcaacaata ggagtggagt    480

gtctgaagag agagcacaga gatttgcgat gatagcagga tctctccctc gggcatgcag    540

caacggcacc ccgttcgtca cagccggggc tgaagatgat gcaccagaag acatcaccga    600

taccctggag aggatcctct ctatccaggc tcaagtatgg gtcacagtag caaaagccat    660

gactgcgtat gagactgcag atgagtcgga aacaaggcga atcaataagt atatgcagca    720

aggcagggtc caaaagaaat acatcctcta ccccgtatgc aggagcacaa tccaactcac    780

gatcagacag tctcttgcag tccgcatctt tttggttagc gagctcaaga gaggccgcaa    840

cacggcaggt ggtacctcta cttattataa cctagtaggg gacgtagact catatatcag    900

gaataccggg cttactgcat tcttcttgac actcaagtac ggaatcaaca ccaagacatc    960

agcccttgca cttagtagcc tctcaggcga catccagaag atgaagcagc tcatgcgttt   1020

gtatcggatg aaaggagata atgcgccgta catgacatta cttggtgata gtgaccagat   1080

gagctttgcg cctgccgagt atgcacaact ttactccttt gccatgggta tggcatcagt   1140

cctagataaa ggtactggga aataccaatt tgccagggac tttatgagca catcattctg   1200

gagacttgga gtagagtacg ctcaggctca gggaagtagc attaacgagg atatggctgc   1260

cgagctaaag ctaaccccgg cagcaaggag ggcctggca gctgctgccc aacgagtctc   1320

cgaggtgacc agcagcatag acatgcctac tcaacaagtc ggagtcctca ctgggcttag   1380

cgaggggga tcccaagccc tacaaggcgg atcgaataga tcgcaagggc aaccagaagc   1440

cggggatggg gagacccaat tcctggatct gatgagagcg gtagcaaata gcatgaggga   1500
```

```
ggcgccaaac tctgcacagg gcactcccca atcggggcct cccccaactc ctgggccatc   1560
ccaagataac gacaccgact gggggtattg attgacaaaa cccagcctgc ttctacaaga   1620
acatcccaat gctctcaccc gtagtcgacc cctcgatttg cggctctata tgaccacacc   1680
ctcaaacaaa catcccctc tttcctccct cccctgctg tacaactccg cacgccctag   1740
ataccacagg cacaccgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacagg gcaagaccaa ggtgctgagc gcagcatggg   2040
agaagcatgg gagcatccag ccaccggcca gtcaagacaa cctcgatcga caggacagat   2100
ctgacaaaca accatccaca cccgagcaaa cgaccccgca cgacagcccg ccggccacat   2160
ccgctgacca gcccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagagg ggaatcacca acgtccgact caacagcagg   2340
ggagtcaacc cagtcgcgga aacagccagg aaagactgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
gggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
catctcccta tgtgatacaa ggaggcgaaa tggcacttaa taaactttcg caaccagtgc   2880
cacatccatc tgaattgatt aaacccgcca ctgcatgcgg gcctgatata ggagtggaga   2940
gggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctagaag cggcaatcct   3180
ctctcgcttc ctcagcccca ctgaatgatc gcgtaaccgt aattaatcta gctacattaa   3240
ggattaagaa aaaatacggg tagaattgga gtgccccaat tgtgccaaga tggactcatc   3300
taggacaatt gggctgtact ttgattctgc ccattcttct agcaacctgt tagcatttcc   3360
gatcgtccta caagacacag gagatgggaa gaagcaaatc gccccgcaat ataggatcca   3420
gcgccttgac tcgtggactg atagtaagga agactcagta ttcatcacca cctatggatt   3480
catctttcaa gttgggaatg aggaagccac tgtcggcatg atcgatgata aacccaagcg   3540
cgagttactt tccgctgcga tgctctgcct aggaagcgtc ccaaataccg gagaccttgt   3600
tgagctggca agggcctgtc tcactatgat ggtcacatgc aagaagagtg caactaatac   3660
tgagagaatg gttttctcag tagtgcaggc accccaagtg ctgcaaagct gtagggttgt   3720
ggcaaataaa tactcatcag tgaatgcagt caagcacgtg aaagcgccag agaagatccc   3780
cgggagtgga accctagaat acaaggtgaa ctttgtctcc ttgactgtgg taccgaagaa   3840
```

-continued

```
ggatgtctac aagatcccag ctgcagtatt gaagatttct ggctcgagtc tgtacaatct   3900
tgcgctcaat gtcactatta atgtggaggt agacccgagg agtcctttgg ttaaatctct   3960
gtctaagtct gacagcggat actatgctaa cctcttcttg catattggac ttatgaccac   4020
cgtagatagg aaggggaaga aagtgacatt tgacaagctg gaaaagaaaa taaggagcct   4080
tgatctatct gtcgggctca gtgatgtgct cgggccttcc gtgttggtaa aagcaagagg   4140
tgcacggact aagcttttgg cacctttctt ctctagcagt gggacagcct gctatcccat   4200
agcaaatgct tctcctcagg tggccaagat actctggagt caaaccgcgt gcctgcggag   4260
cgttaaaatc attatccaag caggtaccca acgcgctgtc gcagtgaccg ctgaccacga   4320
ggttacctct actaagctgg agaaggggca cacccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtcc atcaagttag aaaaaacacg   4500
ggtagaagat tctggatccc ggttggcgcc ctccaggtgc aggatgggct ccagaccttc   4560
taccaagaac ccagcaccta tgatgctgac tatccgggtc gcgctggtac tgagttgcat   4620
ctgcccggca aactccattg atggcaggcc tcttgcagct gcaggaattg tggttacagg   4680
agacaaagca gtcaacatat acacctcatc ccagacagga tcaatcatag ttaagctcct   4740
cccgaatctg cccaaggata aggaggcatg tgcgaaagcc cccttggatg catacaacag   4800
gacattgacc actttgctca cccccccttgg tgactctatc cgtaggatac aagagtctgt   4860
gactacatct ggaggggga gacaggggcg ccttataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cgcaactagc agtggcagtt gggaagatgc agcagtttgt   5100
taatgaccaa tttaataaaa cagctcagga attagactgc atcaaaattg cacagcaagt   5160
tggtgtagag ctcaacctgt acctaaccga attgactaca gtattcggac cacaaatcac   5220
ttcacctgcc ttaaacaagc tgactattca ggcactttac aatctagctg gtgggaatat   5280
ggattactta ttgactaagt taggtatagg gaacaatcaa ctcagctcat taatcggtag   5340
cggcttaatc accggtaacc ctattctata cgactcacag actcaactct tgggtataca   5400
ggtaactcta ccttcagtcg ggaacctaaa taatatgcgt gccacctact tggaaacctt   5460
atccgtaagc acaaccaggg gatttgcctc ggcacttgtc ccaaaagtgg tgacacaggt   5520
cggttctgtg atagaagaac ttgacacctc atactgtata gaaactgact tagatttata   5580
ttgtacaaga atagtaacgt tccctatgtc ccctggtatt tactcctgct tgagcggcaa   5640
tacatcggcc tgtatgtact caaagaccga aggcgcactt actacaccat atatgactat   5700
caaaggctca gtcatcgcta actgcaagat gacaacatgt agatgtgtaa accccccggg   5760
tatcatatcg caaaactatg gagaagccgt gtctctaata gataaacaat catgcaatgt   5820
tttatcctta ggcgggataa ctttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
aaaactagac aaagtcaatg tcaaactgac cagcacatct gctctcatta cctatatcgt   6060
tttgactatc atatctcttg tttttggtat acttagcctg attctagcat gctacctaat   6120
gtacaagcaa aaggcgcaac aaaagacctt attatggctt gggaataata ccctagatca   6180
gatgagagcc actacaaaaa tgtgaacaca gatgaggaac gaaggtttcc ctaatagtaa   6240
```

```
tttgtgtgaa agttctggta gtctgtcagt tcggagagtt aagaaaaaac taccggttgt   6300
agatgaccaa aggacgatat acgggtagaa cggtaagaga ggccgcccct caattgcgag   6360
ccagacttca caacctccgt tctaccgctt caccgacaac agtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatgggggc tagcacacct agcgatcttg taggcatacc gactaggatt   6600
tccagggcag aagaaaagat tacatctaca cttggttcca atcaagatgt agtagatagg   6660
atatataagc aagtggccct tgagtctcca ttggcattgt taaatactga gaccacaatt   6720
atgaacgcaa taacatctct ctcttatcag attaatggag ctgcaaacaa cagcgggtgg   6780
ggggcaccta ttcatgaccc agattatata ggggggatag gcaaagaact cattgtagat   6840
gatgctagtg atgtcacatc attctatccc tctgcatttc aagaacatct gaattttatc   6900
ccggcgccta ctacaggatc aggttgcact cgaataccct catttgacat gagtgctacc   6960
cattactgct acacccataa tgtaatattg tctggatgca gagatcactc acactcacat   7020
cagtatttag cacttggtgt gctccggaca tctgcaacag ggagggtatt cttttctact   7080
ctgcgttcca tcaacctgga cgacacccaa aatcggaagt cttgcagtgt gagtgcaact   7140
cccctgggtt gtgatatgct gtgctcgaaa gccacggaga cagaggaaga agattataac   7200
tcagctgtcc ctacgcggat ggtacatggg aggttagggt tcgacggcca atatcacgaa   7260
aaggacctag atgtcacaac attattcggg gactgggtgg ccaactaccc aggagtaggg   7320
ggtggatctt ttattgacag ccgcgtatgg ttctcagtct acggagggtt aaaacccaat   7380
acacccagtg acactgtaca ggaagggaaa tatgtgatat acaagcgata caatgacaca   7440
tgcccagatg agcaagacta ccagattcga atggccaagt cttcgtataa gcctggacgg   7500
tttggtggga aacgcataca gcaggctatc ttatctatca aagtgtcaac atccttaggc   7560
gaagacccgg tactgactgt accgcccaac acagtcacac tcatgggggc cgaaggcaga   7620
attctcacag tagggacatc ccatttcttg tatcagcgag ggtcatcata cttctctccc   7680
gcgttattat atcctatgac agtcagcgac aaaacagcca ctcttcatag tccttataca   7740
ttcaatgcct tcactcggcc aggtagtatc ccttgccagg cttcagcaag atgccccaac   7800
tcgtgtgtta ctggagtcta tacagatcca tatcccctaa tcttctatag aaaccacacc   7860
ttgcgagggg tattcgggac aatgcttgat ggtgaacaag caagacttaa ccctgcgtct   7920
gcagtattcg atagcacatc ccgcagtcgc ataactcgag tgagttcaag cagcatcaaa   7980
gcagcataca caacatcaac ttgttttaaa gtggtcaaga ccaataagac ctattgtctc   8040
agcattgctg aaatatctaa tactctcttc ggagaattca gaatcgtccc gttactagtt   8100
gagatcctca aagatgacgg ggttagagaa gccaggtctg gctagttgag tcaactatga   8160
aagagttgga aagatggcat tgtatcacct atcttctgcg acatcaagaa tcaaaccgaa   8220
tgccggcgcg tgctcgaatt ccatgtcgcc agttgaccac aatcagccag tgctcatgcg   8280
atcagattaa gccttgtcaa tagtctcttg attaagaaaa aatgtaagtg gcaatgagat   8340
acaaggcaaa acagctcacg gtaaataata cgggtaggac atggcgagct ccggtcctga   8400
aagggcagag catcagatta tcctaccaga gtcacacctg tcttcaccat tggtcaagca   8460
caaactactc tattattgga aattaactgg gctaccgctt cctgatgaat gtgacttcga   8520
ccacctcatt ctcagccgac aatggaaaaa aatacttgaa tcggcctctc ctgatactga   8580
```

```
gagaatgata aaactcggaa gggcagtaca ccaaactctt aaccacaatt ccagaataac   8640
cggagtactc caccccaggt gtttagaaga actggctaat attgaggtcc ctgattcaac   8700
caacaaattt cggaagattg agaagaagat ccaaattcac aacacgagat atggagaact   8760
gttcacaagg ctgtgtacgc atatagagaa gaaactgctg ggtcatcttt ggtctaacaa   8820
tgtcccccgg tcagaggagt tcagcagcat tcgtacggat ccggcattct ggtttcactc   8880
aaaatggtcc acagccaagt ttgcatggct ccatataaaa cagatccaga ggcatctgat   8940
tgtggcagct aggacaaggt ctgcggccaa caaattggtg atgctaaccc ataaggtagg   9000
ccaagtcttt gtcactcctg aacttgttgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
gggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgcctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacggat acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atacgaccct gtcactaacc tgagcatgtt   9780
cctaaaagac aaggcaatcg cacaccccaa cgataattgg cttgcctcgt ttaggcggaa   9840
ccttctctcc gaagaccaga agaaacatgt aaaggaagcg acttcgacta accgcctctt   9900
gatagagttt ttagagtcaa atgattttga tccatataaa gagatggaat atctgacgac   9960
ccttgagtac cttagagatg acaatgtggc agtatcatac tcgctcaaag agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatgttca aaccgcaatc atgatccgaa  10260
aagcaagaac cgtcggagag ttgcaacctt cataacaact gacctgcaaa agtactgtct  10320
taattggaga tatcagacga tcaaattgtt cgctcatgcc atcaatcagt tgatgggcct  10380
acctcatttc ttcgagtgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag atgactctcc  10680
ggagatggtg ttgacacagt tgcatcaagc cagtgataat ttcttcaagg aattaatcca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa aacaccgtaa tgtcctgtgc  10920
caacattgcc tctactgtag cacggctatg cgagaacggg cttcccaaag acttctgtta  10980
```

```
ctatttaaac tatataatga gttgtgtgca gacatacttt gactctgagt tctccatcac  11040
caacaattcg caccccgatc ttaatcagtc gtggattgag gacatctctt ttgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggacta ctgagtccta acattaggac taatatctta actaggccgc ctgggaatgg  11280
agattgggcc agtctgtgca acgacccata ctctttcaat tttgagactg ttgcaagccc  11340
aaacattgtt cttaagaaac atacgcaaag agtcctattt gaaacttgtt caaatccctt  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacactgtaa ttaagattgc  11580
gcttactagg aggccattag gcatcaagag gctgatgcgg atagtcaatt attctagcat  11640
gcatgcaatg ctgtttagag acgatgtttt ttcctctagt agatccaacc accccttagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
gggtgagatt cttagtgtaa gcggagggtg tacaagatgt gacagcggag atgaacaatt  11880
tacttggttc catcttccaa gcaatataga attgaccgat gacaccagca agaatcctcc  11940
gatgagggta ccatatctcg ggtcaaagac acaggagagg agagctgcct cacttgcgaa  12000
aatagctcat atgtcgccac atgtgaaggc tgccctaagg gcatcatccg tgttgatctg  12060
ggcttatggg gataatgaag taaattggac tgctgctctt acgattgcaa aatctcggtg  12120
taatgtaaac ttagagtatc ttcggttact gtccccttta cccacggctg ggaatcttca  12180
acatagacta gatgatggta taactcagat gacattcacc cctgcatctc tctacagggt  12240
gtcaccttac attcacatat ccaatgattc tcaaaggctg ttcactgaag aaggagtcaa  12300
agaggggaat gtggtttacc aacagatcat gctcttgggt ttatctctaa tcgaatcgat  12360
ctttccaatg acaacaacca gaacatatga tgagatcaca ctgcacctac atagtaaatt  12420
tagttgctgt atcagggaag cacctgttgc ggttcctttc gagctacttg ggtggcaccc  12480
ggaactgagg acagtgacct caaataagtt tatgtatgat cctagccctg tatcggaggg  12540
agactttgcg agacttgact tagctatctt caagagttat gagcttaatc tggagtcata  12600
tcccacgata gagctaatga acattctttc aatatccagc gggaagttga ttggccagtc  12660
tgtggtttct tatgatgaag atacctccat aaagaatgat gccataatag tgtatgacaa  12720
tacccgaaat tggatcagtg aagctcagaa ttcagatgtg gtccgcctat ttgaatatgc  12780
agcacttgaa gtgctcctcg actgttctta ccaactctat tacctgagag taagagacct  12840
agacaatatt gtcttatata tgggtgattt atacaagaat atgccaggaa ttctactttc  12900
caacattgca gctacaatat ctcatcctgt cattcattca aggttacatg cagtgggcct  12960
ggtcaaccat gacggatcac accaacttgc agatacggat tttatcgaaa tgtctgcaaa  13020
actgttagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
```

cccagctaat ctgtactaca tgtctcggaa gagcctcaat ttgatcaggg aaagggagga 13380
cagggatact atcctggcgt tgttgttccc ccaagagcca ttattagagt tcccttctgt 13440
gcaagatatt ggtgctcgag tgaaagatcc attcacccga caacctgcgg catttttgca 13500
agagttagat ttgagtgctc cagcaaggta tgacgcattc acacttagtc agattcatcc 13560
tgaactcaca tctccaaatc cggaggaaga ctacttagta cgatacttgt tcagagggat 13620
agggactgca tcttcctctt ggtataaggc atcccatctc ctttctgtac ccgaggtaag 13680
atgtgcaaga cacgggaact ccttatactt ggctgaagga agcggagcca tcatgagtct 13740
tcttgaactg catgtaccac atgaaactat ctattacaat acgctctttt caaatgagat 13800
gaaccccccg caacgacatt tcgggccgac ccccaactcag tttttgaatt cggttgttta 13860
taggaatcta caggcggagg taacatgcaa ggatggattt gtccaagagt tccgtccatt 13920
atggagagaa aatacagagg aaagtgacct gacctcagat aaagcagtgg ggtatattac 13980
atctgcagta ccctacagat ctgtatcatt gctgcattgt gacattgaaa ttcctccagg 14040
gtccaatcaa agcttactag atcaactagc tatcaattta tctctgattg ccatgcattc 14100
tgtaagggag ggcggggtag taatcatcaa agtgttgtat gcaatgggat actactttca 14160
tctactcatg aacttgtttg ctccgtgttc cacaaaagga tatattctct ctaatggtta 14220
tgcatgtcga ggggatatgg agtgttacct ggtatttgtc atgggttacc tgggcgggcc 14280
tacatttgta catgaggtgg tgaggatggc aaaaactctg gtgcagcggc acggtacgct 14340
tttgtctaaa tcagatgaga tcacactgac caggttattc acctcacagc ggcagcgtgt 14400
gacagacatc ctatccagtc ctttaccaag attaataaag tacttgagga agaatattga 14460
cactgcgctg attgaagccg ggggacagcc cgtccgtcca ttctgtgcgg agagtctggt 14520
gagcacgcta gcgaacataa ctcagataac ccagatcatc gctagtcaca ttgacacagt 14580
catccggtct gtgatatata tggaagctga gggtgatctc gctgacacag tatttctatt 14640
taccccttac aatctctcta ctgacgggaa aaagaggaca tcacttaaac agtgcacgag 14700
acagatccta gaggttacaa tactaggtct tagagtcgaa aatctcaata aaataggcga 14760
tataatcagc ctagtgctta aaggcatgat ctccatggag gaccttatcc cactaaggac 14820
atacttgaag catagtacct gccctaaata tttgaaggct gtcctaggta ttaccaaact 14880
caaagaaatg tttacagaca cttctgtact gtacttgact cgtgctcaac aaaaattcta 14940
catgaaaact ataggcaatg cagtcaaagg atattacagt aactgtgact cctaacgaaa 15000
atcacatatt aataggctcc ttttttggcc aattgtattc ttgttgattt aattatatta 15060
tgttagaaaa aagttgaact ctgactcctt aggactcgaa ttcgaactca aataaatgtc 15120
tttaaaaaag gttgcgcaca attattcttg agtgtagtct cgtcattcac caaatctttg 15180
tttggt 15186

<210> SEQ ID NO 5
<211> LENGTH: 1992
<212> TYPE: DNA
<213> ORGANISM: Newcastle disease virus

<400> SEQUENCE: 5
acgggtagaa cggtaagaga ggccgcccct caattgcgag ccagacttca caacctccgt 60
tctaccgctt caccgacaac agtcctcaat catggaccgc gccgttagcc aagttgcgtt 120
agagaatgat gaaagagagg caaaaaatac atggcgcttg atattccgga ttgcaatctt 180
attcttaaca gtagtgacct tggctatatc tgtagcctcc cttttatata gcatgggggc 240

```
tagcacacct agcgatcttg taggcatacc gactaggatt tccagggcag aagaaaagat    300

tacatctaca cttggttcca atcaagatgt agtagatagg atatataagc aagtggccct    360

tgagtctcca ttggcattgt taaatactga gaccacaatt atgaacgcaa taacatctct    420

ctcttatcag attaatggag ctgcaaacaa cagcgggtgg ggggcaccta ttcatgaccc    480

agattatata ggggggatag gcaaagaact cattgtagat gatgctagtg atgtcacatc    540

attctatccc tctgcatttc aagaacatct gaattttatc ccggcgccta ctacaggatc    600

aggttgcact cgaatacct catttgacat gagtgctacc cattactgct acacccataa    660

tgtaatattg tctggatgca gagatcactc acactcatat cagtatttag cacttggtgt    720

gctccggaca tctgcaacag ggagggtatt cttttctact ctgcgttcca tcaacctgga    780

cgacacccaa aatcggaagt cttgcagtgt gagtgcaact cccctgggtt gtgatatgct    840

gtgctcgaaa gccacggaga cagaggaaga agattataac tcagctgtcc ctacgcggat    900

ggtacatggg aggttagggt tcgacggcca atatcacgaa aaggacctag atgtcacaac    960

attattcggg gactgggtgg ccaactaccc aggagtaggg ggtggatctt ttattgacag   1020

ccgcgtatgg ttctcagtct acggagggtt aaaacccaat tcacccagtg acactgtaca   1080

ggaagggaaa tatgtgatat acaagcgata caatgacaca tgcccagatg agcaagacta   1140

ccagattcga atggccaagt cttcgtataa gcctggacgg tttggtggga aacgcataca   1200

gcaggctatc ttatctatca aagtgtcaac atccttaggc gaagacccgg tactgactgt   1260

accgcccaac acagtcacac tcatgggggc cgaaggcaga attctcacag tagggacatc   1320

ccatttcttg tatcagcgag ggtcatcata cttctctccc gcgttattat atcctatgac   1380

agtcagcaac aaaacagcca ctcttcatag tccttataca ttcaatgcct tcactcggcc   1440

aggtagtatc ccttgccagg cttcagcaag atgccccaac tcgtgtgtta ctggagtcta   1500

tacagatcca tatcccctaa tcttctatag aaaccacacc ttgcgagggg tattcgggac   1560

aatgcttgat ggtgaacaag caagacttaa ccctgcgtct gcagtattcg atagcacatc   1620

ccgcagtcgc ataactcgag tgagttcaag cagcatcaaa gcagcataca caacatcaac   1680

ttgttttaaa gtggtcaaga ccaataagac ctattgtctc agcattgctg aaatatctaa   1740

tactctcttc ggagaattca gaatcgtccc gttactagtt gagatcctca aagatgacgg   1800

ggttagagaa gccaggtctg gctagttgag tcaactatga aagagttgga aagatggcat   1860

tgtatcacct atcttctgcg acatcaagaa tcaaaccgaa tgccggcgcg tgctcgaatt   1920

ccatgtcgcc agttgaccac aatcagccag tgctcatgcg atcagattaa gccttgtcaa   1980

tagtctcttg at                                                       1992
```

```
<210> SEQ ID NO 6
<211> LENGTH: 577
<212> TYPE: PRT
<213> ORGANISM: Newcastle disease virus

<400> SEQUENCE: 6

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
```

```
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Ala Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Thr Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asp Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
    450                 455                 460

Cys Val Thr Gly Val Tyr Thr Asp Pro Tyr Pro Leu Ile Phe Tyr Arg
465                 470                 475                 480
```

```
Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ser Ile Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly


<210> SEQ ID NO 7
<211> LENGTH: 1782
<212> TYPE: DNA
<213> ORGANISM: Newcastle disease virus

<400> SEQUENCE: 7

acgggtagaa gactctggat cccggttggc gccctccagg tgcaggatgg gctccagacc     60

ttttaccaag aacccagcac ctatgatgct gactatccgg gtcgcgctgg tattgagttg    120

catctgtccg gcaaactcca ttgatggcag gccttttgca gctgcaggaa ttgtggttac    180

aggagacaaa gcagtcaaca tatacacctc atcccagaca ggatcaatca tagttaagct    240

cctcccgaat ctgcccaagg ataaggaggc atgtgcgaaa gccccccttgg atgcatacaa    300

caggacattg accactttgc tcacccccct tggtgactct atccgtagga tacaagagtc    360

tgtgactaca tctggagggg ggagacaggg gcgccttata ggcgccatta ttggcggtgt    420

ggctcttggg gttgcaactg ccgcacaaat aacagcggcc gcagctctga tacaagccaa    480

acaaaatgct gccaacatcc tccgacttaa agagagcatt gccgcaacca atgaggctgt    540

gcatgaggtc actgacggat tatcccaact agcagtggca gttgggaaga tgcagcagtt    600

tgttaatgac caatttaata aaacagctca ggaattagac tgcataaaaa ttgcacagca    660

agttggtgta gagctcaacc tgtacctaac cgaattgact acagtattcg gaccacaaat    720

cacttcacct gccttaaaca agctgactat tcaggcactt tacaatctag ctggtgggaa    780

tatggattac ttattgacta agttaggtat agggaacaat caactcagct cattaatcgg    840

tagcggctta atcaccggta accctattct atacgactca cagactcaac tcttgggtat    900

acaggtaact ctaccttcag tcgggaacct aaataatatg cgtgccacct acttggaaac    960

cttatccgta agcacaacca ggggatttgc ctcggcactt gtcccaaaag tggtgacaca   1020

ggtcggttct gtgatagaag aacttgacac ctcatactgt atagaaactg acttagattt   1080

atattgtaca agaatagtaa cgttccctat gtcccctggt atttactcct gcttgagcgg   1140

caatacatcg gcctgtatgt actcaaagac cgaaggcgca cttactacac catatatgac   1200

tatcaaaggc tcagtcatcg ctaactgcaa gatgacaaca tgtagatgtg taaacccccc   1260

gggtatcata tcgcaaaact atggagaagc cgtgtctcta atagataaac aatcatgcaa   1320

tgttttatcc ttaggcggga taactttaag gctcagtggg gaattcgatg taacttatca   1380

gaagaatatc tcaatacaag attctcaagt aataataaca ggcaatcttg atatctcaac   1440

tgagcttggg aatgtcaaca actcgatcag taatgctttg aataagttag aggaaagcaa   1500
```

```
cagaaaacta gacaaagtca atgtcaaact gaccagcaca tctgctctca ttacctatat   1560

cgttttgact atcatatctc ttgtttttgg tatacttagc ctgattctag catgctacct   1620

aatgtacaag caaaaggcgc aacaaaagac cttattatgg cttgggaata ataccctaga   1680

tcagatgaga gccactacaa aaatgtgaac acagatgagg aacgaaggtt tccctaatag   1740

taatttgtgt gaaagttctg gtagtctgtc agttcggaga gt                      1782


<210> SEQ ID NO 8
<211> LENGTH: 553
<212> TYPE: PRT
<213> ORGANISM: Newcastle disease virus

<400> SEQUENCE: 8

Met Gly Ser Arg Pro Phe Thr Lys Asn Pro Ala Pro Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Phe Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
```

```
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

```
<210> SEQ ID NO 9
<211> LENGTH: 1662
<212> TYPE: DNA
<213> ORGANISM: Artificial Sequence
<220> FEATURE:
<223> OTHER INFORMATION: NDV F3aa-modified fusion protein

<400> SEQUENCE: 9

atgggctcca gaccttctac caagaaccca gcacctatga tgctgactat ccgggtcgcg      60

ctggtactga gttgcatctg cccggcaaac tccattgatg gcaggcctct tgcagctgca     120

ggaattgtgg ttacaggaga caaagcagtc aacatataca cctcatccca gacaggatca     180

atcatagtta agctcctccc gaatctgccc aaggataagg aggcatgtgc gaaagccccc     240

ttggatgcat acaacaggac attgaccact ttgctcaccc cccttggtga ctctatccgt     300

aggatacaag agtctgtgac tacatctgga gggcggagac agaggcgctt tataggcgcc     360

attattggcg gtgtggctct tggggttgca actgccgcac aaataacagc ggccgcagct     420

ctgatacaag ccaaacaaaa tgctgccaac atcctccgac ttaaagagag cattgccgca     480

accaatgagg ctgtgcatga ggtcactgac ggattatcgc aactagcagt ggcagttggg     540

aagatgcagc agtttgttaa tgaccaattt aataaaacag ctcaggaatt agactgcatc     600

aaaattgcac agcaagttgg tgtagagctc aacctgtacc taaccgaatt gactacagta     660

ttcggaccac aaatcacttc acctgcctta aacaagctga ctattcaggc actttacaat     720

ctagctggtg ggaatatgga ttacttattg actaagttag gtatagggaa caatcaactc     780
```

```
agctcattaa tcggtagcgg cttaatcacc ggtaacccta ttctatacga ctcacagact    840

caactcttgg gtatacaggt aactctacct tcagtcggga acctaaataa tatgcgtgcc    900

acctacttgg aaaccttatc cgtaagcaca accaggggat ttgcctcggc acttgtccca    960

aaagtggtga cacaggtcgg ttctgtgata gaagaacttg acacctcata ctgtatagaa   1020

actgacttag atttatattg tacaagaata gtaacgttcc ctatgtcccc tggtatttac   1080

tcctgcttga gcggcaatac atcggcctgt atgtactcaa agaccgaagg cgcacttact   1140

acaccatata tgactatcaa aggctcagtc atcgctaact gcaagatgac aacatgtaga   1200

tgtgtaaacc ccccgggtat catatcgcaa aactatggag aagccgtgtc tctaatagat   1260

aaacaatcat gcaatgtttt atccttaggc gggataactt taaggctcag tggggaattc   1320

gatgtaactt atcagaagaa tatctcaata caagattctc aagtaataat aacaggcaat   1380

cttgatatct caactgagct tgggaatgtc aacaactcga tcagtaatgc tttgaataag   1440

ttagaggaaa gcaacagaaa actagacaaa gtcaatgtca aactgaccag cacatctgct   1500

ctcattacct atatcgtttt gactatcata tctcttgttt ttggtatact tagcctgatt   1560

ctagcatgct acctaatgta caagcaaaag gcgcaacaaa agaccttatt atggcttggg   1620

aataataccc tagatcagat gagagccact acaaaaatgt ga                      1662


<210> SEQ ID NO 10
<211> LENGTH: 553
<212> TYPE: PRT
<213> ORGANISM: Artificial Sequence
<220> FEATURE:
<223> OTHER INFORMATION: NDV F3aa-modified fusion protein

<400> SEQUENCE: 10

Met Gly Ser Arg Pro Phe Thr Lys Asn Pro Ala Pro Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Phe Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
            100                 105                 110

Arg Gln Arg Arg Phe Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205
```

```
Glu Leu Asn Leu Tyr Leu Thr Glu Leu Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

<210> SEQ ID NO 11
<211> LENGTH: 1662
<212> TYPE: DNA
<213> ORGANISM: Artificial Sequence
<220> FEATURE:
<223> OTHER INFORMATION: NDV F3aa-modified fusion protein with L289A

<400> SEQUENCE: 11

```
atgggctcca gaccttctac caagaaccca gcacctatga tgctgactat ccgggtcgcg      60
```

```
ctggtactga gttgcatctg cccggcaaac tccattgatg gcaggcctct tgcagctgca    120

ggaattgtgg ttacaggaga caaagcagtc aacatataca cctcatccca gacaggatca    180

atcatagtta agctcctccc gaatctgccc aaggataagg aggcatgtgc gaaagccccc    240

ttggatgcat acaacaggac attgaccact ttgctcaccc cccttggtga ctctatccgt    300

aggatacaag agtctgtgac tacatctgga gggcggagac agaggcgctt tataggcgcc    360

attattggcg gtgtggctct tggggttgca actgccgcac aaataacagc ggccgcagct    420

ctgatacaag ccaaacaaaa tgctgccaac atcctccgac ttaaagagag cattgccgca    480

accaatgagg ctgtgcatga ggtcactgac ggattatcgc aactagcagt ggcagttggg    540

aagatgcagc agtttgttaa tgaccaattt aataaaacag ctcaggaatt agactgcatc    600

aaaattgcac agcaagttgg tgtagagctc aacctgtacc taaccgaatt gactacagta    660

ttcggaccac aaatcacttc acctgcctta aacaagctga ctattcaggc actttacaat    720

ctagctggtg ggaatatgga ttacttattg actaagttag gtatagggaa caatcaactc    780

agctcattaa tcggtagcgg cttaatcacc ggtaacccta ttctatacga ctcacagact    840

caactcttgg gtatacaggt aactgcacct tcagtcggga acctaaataa tatgcgtgcc    900

acctacttgg aaaccttatc cgtaagcaca accaggggat ttgcctcggc acttgtccca    960

aaagtggtga cacaggtcgg ttctgtgata gaagaacttg acacctcata ctgtatagaa   1020

actgacttag atttatattg tacaagaata gtaacgttcc ctatgtcccc tggtatttac   1080

tcctgcttga gcggcaatac atcggcctgt atgtactcaa agaccgaagg cgcacttact   1140

acaccatata tgactatcaa aggctcagtc atcgctaact gcaagatgac aacatgtaga   1200

tgtgtaaacc ccccgggtat catatcgcaa aactatggag aagccgtgtc tctaatagat   1260

aaacaatcat gcaatgtttt atccttaggc gggataactt taaggctcag tggggaattc   1320

gatgtaactt atcagaagaa tatctcaata caagattctc aagtaataat aacaggcaat   1380

cttgatatct caactgagct tgggaatgtc aacaactcga tcagtaatgc tttgaataag   1440

ttagaggaaa gcaacagaaa actagacaaa gtcaatgtca aactgaccag cacatctgct   1500

ctcattacct atatcgtttt gactatcata tctcttgttt ttggtatact tagcctgatt   1560

ctagcatgct acctaatgta caagcaaaag gcgcaacaaa agaccttatt atggcttggg   1620

aataataccc tagatcagat gagagccact acaaaaatgt ga                      1662
```

<210> SEQ ID NO 12
<211> LENGTH: 553
<212> TYPE: PRT
<213> ORGANISM: Artificial Sequence
<220> FEATURE:
<223> OTHER INFORMATION: NDV F3aa-modified fusion protein with L289A

<400> SEQUENCE: 12

```
Met Gly Ser Arg Pro Phe Thr Lys Asn Pro Ala Pro Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Phe Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80
```

```
Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
            100                 105                 110

Arg Gln Arg Arg Phe Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Ala Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
```

```
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550


<210> SEQ ID NO 13
<211> LENGTH: 13006
<212> TYPE: DNA
<213> ORGANISM: Artificial Sequence
<220> FEATURE:
<223> OTHER INFORMATION: Virus/vector construct

<400> SEQUENCE: 13

acgaagacaa acaaaccatt attatcatta aaaggctcag gagaaacttt aacagtaatc      60

aaaatgtctg ttacagtcaa gagaatcatt gacaacacag tcgtagttcc aaaacttcct     120

gcaaatgagg atccagtgga atacccggca gattacttca gaaaatcaaa ggagattcct     180

ctttacatca atactacaaa aagtttgtca gatctaagag gatatgtcta ccaaggcctc     240

aaatccggaa atgtatcaat catacatgtc aacagctact tgtatggagc attaaaggac     300

atccggggta agttggataa agattggtca agtttcggaa taaacatcgg gaaagcaggg     360

gatacaatcg gaatatttga ccttgtatcc ttgaaagccc tggacggcgt acttccagat     420

ggagtatcgg atgcttccag aaccagcgca gatgacaaat ggttgccttt gtatctactt     480

ggcttataca gagtgggcag aacacaaatg cctgaataca gaaaaaagct catggatggg     540

ctgacaaatc aatgcaaaat gatcaatgaa cagtttgaac ctcttgtgcc agaaggtcgt     600

gacatttttg atgtgtgggg aaatgacagt aattacacaa aaattgtcgc tgcagtggac     660

atgttcttcc acatgttcaa aaaacatgaa tgtgcctcgt tcagatacgg aactattgtt     720

tccagattca aagattgtgc tgcattggca acatttggac acctctgcaa aataaccgga     780

atgtctacag aagatgtaac gacctggatc ttgaaccgag aagttgcaga tgaaatggtc     840

caaatgatgc ttccaggcca agaaattgac aaggccgatt catacatgcc ttatttgatc     900

gactttggat tgtcttctaa gtctccatat tcttccgtca aaaaccctgc cttccacttc     960

tgggggcaat tgacagctct tctgctcaga tccaccagag caaggaatgc ccgacagcct    1020

gatgacattg agtatacatc tcttactaca gcaggtttgt tgtacgctta tgcagtagga    1080

tcctctgccg acttggcaca acagttttgt gttggagata acaaatacac tccagatgat    1140

agtaccggag gattgacgac taatgcaccg ccacaaggca gagatgtggt cgaatggctc    1200

ggatggtttg aagatcaaaa cagaaaaccg actcctgata tgatgcagta tgcgaaaaga    1260

gcagtcatgt cactgcaagg cctaagagag aagacaattg gcaagtatgc taagtcagaa    1320

tttgacaaat gaccctataa ttctcagatc acctattata tattatgcta catatgaaaa    1380

aaactaacag atatcatgga taatctcaca aaagttcgtg agtatctcaa gtcctattct    1440

cgtctggatc aggcggtagg agagatagat gagatcgaag cacaacgagc tgaaaagtcc    1500

aattatgagt tgttccaaga ggatggagtg gaagagcata ctaagccctc ttattttcag    1560

gcagcagatg attctgacac agaatctgaa ccagaaattg aagacaatca aggcttgtat    1620

gcaccagatc cagaagctga gcaagttgaa ggctttatac aggggccttt agatgactat    1680

gcagatgagg aagtggatgt tgtatttact tcggactgga aacagcctga gcttgaatct    1740
```

```
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaaagtaa cagatatcac   2220
gatctaagtg ttatcccaat ccattcatca tgagttcctt aaagaagatt ctcggtctga   2280
aggggaaagg taagaaatct aagaaattag ggatcgcacc acccccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga aacgtccctt ctacaaaatc ttggcttttt   2580
tgggttcttc taatctaaag gccactccag cggtattggc agatcaaggt caaccagagt   2640
atcacgctca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctggactc tatcggccac ttcaaatgag   2940
ctagtctaac ttctagcttc tgaacaatcc ccggtttact cagtctcccc taattccagc   3000
ctctcgaaca actaatatcc tgtctttttct atccctatga aaaaaactaa cagagatcga   3060
tctgtttacg cgtcgagatg ggctccagac cttctaccaa gaacccagca cctatgatgc   3120
tgactatccg ggtcgcgctg gtactgagtt gcatctgccc ggcaaactcc attgatggca   3180
ggcctcttgc agctgcagga attgtggtta caggagacaa agcagtcaac atatacacct   3240
catcccagac aggatcaatc atagttaagc tcctcccgaa tctgcccaag gataaggagg   3300
catgtgcgaa agccccccttg gatgcataca acaggacatt gaccactttg ctcacccccc   3360
ttggtgactc tatccgtagg atacaagagt ctgtgactac atctggaggg cggagacaga   3420
ggcgctttat aggcgccatt attggcggtg tggctcttgg ggttgcaact gccgcacaaa   3480
taacagcggc cgcagctctg atacaagcca aacaaaatgc tgccaacatc ctccgactta   3540
aagagagcat tgccgcaacc aatgaggctg tgcatgaggt cactgacgga ttatcgcaac   3600
tagcagtggc agttgggaag atgcagcagt ttgttaatga ccaatttaat aaaacagctc   3660
aggaattaga ctgcatcaaa attgcacagc aagttggtgt agagctcaac ctgtacctaa   3720
ccgaattgac tacagtattc ggaccacaaa tcacttcacc tgccttaaac aagctgacta   3780
ttcaggcact ttacaatcta gctggtggga atatggatta cttattgact aagttaggta   3840
tagggaacaa tcaactcagc tcattaatcg gtagcggctt aatcaccggt aaccctattc   3900
tatacgactc acagactcaa ctcttgggta tacaggtaac tgcaccttca gtcgggaacc   3960
taaataatat gcgtgccacc tacttggaaa ccttatccgt aagcacaacc aggggatttg   4020
cctcggcact tgtcccaaaa gtggtgacac aggtcggttc tgtgatagaa gaacttgaca   4080
cctcatactg tatagaaact gacttagatt tatattgtac aagaatagta acgttcccta   4140
```

```
tgtcccctgg tatttactcc tgcttgagcg gcaatacatc ggcctgtatg tactcaaaga   4200
ccgaaggcgc acttactaca ccatatatga ctatcaaagg ctcagtcatc gctaactgca   4260
agatgacaac atgtagatgt gtaaaccccc cgggtatcat atcgcaaaac tatggagaag   4320
ccgtgtctct aatagataaa caatcatgca atgttttatc cttaggcggg ataactttaa   4380
ggctcagtgg ggaattcgat gtaacttatc agaagaatat ctcaatacaa gattctcaag   4440
taataataac aggcaatctt gatatctcaa ctgagcttgg gaatgtcaac aactcgatca   4500
gtaatgcttt gaataagtta gaggaaagca acagaaaact agacaaagtc aatgtcaaac   4560
tgaccagcac atctgctctc attacctata tcgttttgac tatcatatct cttgtttttg   4620
gtatacttag cctgattcta gcatgctacc taatgtacaa gcaaaaggcg caacaaaaga   4680
ccttattatg gcttgggaat aataccctag atcagatgag agccactaca aaaatgtgag   4740
ctagcttaat taatatgaaa aaaactaaca gatatcatgg accgcgccgt tagccaagtt   4800
gcgttagaga atgatgaaag agaggcaaaa aatacatggc gcttgatatt ccggattgca   4860
atcttattct taacagtagt gaccttggct atatctgtag cctccctttt atatagcatg   4920
ggggctagca cacctagcga tcttgtaggc ataccgacta ggatttccag ggcagaagaa   4980
aagattacat ctacacttgg ttccaatcaa gatgtagtag ataggatata taagcaagtg   5040
gcccttgagt ctccattggc attgttaaat actgagacca caattatgaa cgcaataaca   5100
tctctctctt atcagattaa tggagctgca aacaacagcg ggtggggggc acctattcat   5160
gacccagatt atatagggggg gataggcaaa gaactcattg tagatgatgc tagtgatgtc   5220
acatcattct atccctctgc atttcaagaa catctgaatt ttatcccggc gcctactaca   5280
ggatcaggtt gcactcgaat accctcattt gacatgagtg ctacccatta ctgctacacc   5340
cataatgtaa tattgtctgg atgcagagat cactcacact cacatcagta tttagcactt   5400
ggtgtgctcc ggacatctgc aacagggagg gtattctttt ctactctgcg ttccatcaac   5460
ctggacgaca cccaaaatcg gaagtcttgc agtgtgagtg caactcccct gggttgtgat   5520
atgctgtgct cgaaagccac ggagacagag gaagaagatt ataactcagc tgtccctacg   5580
cggatggtac atgggaggtt agggttcgac ggccaatatc acgaaaagga cctagatgtc   5640
acaacattat tcggggactg ggtggccaac tacccaggag taggggggtgg atcttttatt   5700
gacagccgcg tatggttctc agtctacgga gggttaaaac ccaatacacc cagtgacact   5760
gtacaggaag ggaaatatgt gatatacaag cgatacaatg acacatgccc agatgagcaa   5820
gactaccaga ttcgaatggc caagtcttcg tataagcctg gacggtttgg tgggaaacgc   5880
atacagcagg ctatcttatc tatcaaagtg tcaacatcct taggcgaaga cccggtactg   5940
actgtaccgc ccaacacagt cacactcatg gggggccgaag gcagaattct cacagtaggg   6000
acatcccatt tcttgtatca gcgagggtca tcatacttct ctcccgcgtt attatatcct   6060
atgacagtca gcgacaaaac agccactctt catagtcctt atacattcaa tgccttcact   6120
cggccaggta gtatcccttg ccaggcttca gcaagatgcc ccaactcgtg tgttactgga   6180
gtctatacag atccatatcc cctaatcttc tatagaaacc acaccttgcg aggggtattc   6240
gggacaatgc ttgatggtga acaagcaaga cttaaccctg cgtctgcagt attcgatagc   6300
acatcccgca gtcgcataac tcgagtgagt tcaagcagca tcaaagcagc atacacaaca   6360
tcaacttgtt ttaaagtggt caagaccaat aagacctatt gtctcagcat tgctgaaata   6420
tctaatactc tcttcggaga attcagaatc gtcccgttac tagttgagat cctcaaagat   6480
```

gacggggtta gagaagccag gtctggctag gtttaaacgc tagcggcctc aattatattt 6540
gagtttttaa tttttatgaa aaaaactaac agcaatcatg gaagtccacg attttgagac 6600
cgacgagttc aatgatttca atgaagatga ctatgccaca agagaattcc tgaatcccga 6660
tgagcgcatg acgtacttga atcatgctga ttacaacctg aattctcctc taattagtga 6720
tgatattgac aatttaatca ggaaattcaa ttctcttcca attccctcga tgtgggatag 6780
taagaactgg gatggagttc ttgagatgtt aacgtcatgt caagccaatc ccatcccaac 6840
atctcagatg cataaatgga tgggaagttg gttaatgtct gataatcatg atgccagtca 6900
agggtatagt tttttacatg aagtggacaa agaggcagaa ataacatttg acgtggtgga 6960
gaccttcatc cgcggctggg gcaacaaacc aattgaatac atcaaaaagg aaagatggac 7020
tgactcattc aaaattctcg cttatttgtg tcaaaagttt ttggacttac acaagttgac 7080
attaatctta aatgctgtct ctgaggtgga attgctcaac ttggcgagga ctttcaaagg 7140
caaagtcaga agaagttctc atggaacgaa catatgcagg attagggttc ccagcttggg 7200
tcctactttt atttcagaag gatgggctta cttcaagaaa cttgatattc taatggaccg 7260
aaactttctg ttaatggtca aagatgtgat tatagggagg atgcaaacgg tgctatccat 7320
ggtatgtaga atagacaacc tgttctcaga gcaagacatc ttctcccttc taaatatcta 7380
cagaattgga gataaaattg tggagaggca gggaaatttt tcttatgact tgattaaaat 7440
ggtggaaccg atatgcaact tgaagctgat gaaattagca agagaatcaa ggcctttagt 7500
cccacaattc cctcattttg aaaatcatat caagacttct gttgatgaag ggcaaaaaat 7560
tgaccgaggt ataagattcc tccatgatca gataatgagt gtgaaaacag tggatctcac 7620
actggtgatt tatggatcgt tcagacattg ggtcatcct tttatagatt attacactgg 7680
actagaaaaa ttacattccc aagtaaccat gaagaaagat attgatgtgt catatgcaaa 7740
agcacttgca agtgatttag ctcggattgt tctatttcaa cagttcaatg atcataaaaa 7800
gtggttcgtg aatggagact tgctccctca tgatcatccc tttaaaagtc atgttaaaga 7860
aaatacatgg cccacagctg ctcaagttca agattttgga gataaatggc atgaacttcc 7920
gctgattaaa tgttttgaaa tacccgactt actagaccca tcgataatat actctgacaa 7980
aagtcattca atgaataggt cagaggtgtt gaaacatgtc cgaatgaatc cgaacactcc 8040
tatccctagt aaaaaggtgt tgcagactat gttggacaca aaggctacca attggaaaga 8100
atttcttaaa gagattgatg agaagggctt agatgatgat gatctaatta ttggtcttaa 8160
aggaaaggag agggaactga agttggcagg tagatttttc tccctaatgt cttggaaatt 8220
gcgagaatac tttgtaatta ccgaatattt gataaagact catttcgtcc ctatgtttaa 8280
aggcctgaca atggcggacg atctaactgc agtcattaaa aagatgttag attcctcatc 8340
cggccaagga ttgaagtcat atgaggcaat ttgcatagcc aatcacattg attacgaaaa 8400
atggaataac caccaaagga agttatcaaa cggcccagtg ttccgagtta tgggccagtt 8460
cttaggttat ccatccttaa tcgagagaac tcatgaattt tttgagaaaa gtcttatata 8520
ctacaatgga agaccagact tgatgcgtgt tcacaacaac acactgatca attcaacctc 8580
ccaacgagtt tgttggcaag gacaagaggg tggactggaa ggtctacggc aaaaaggatg 8640
gagtatcctc aatctactgg ttattcaaag agaggctaaa atcagaaaca ctgctgtcaa 8700
agtcttggca caaggtgata atcaagttat ttgcacacag tataaaacga agaaatcgag 8760
aaacgttgta gaattacagg gtgctctcaa tcaaatggtt tctaataatg agaaaattat 8820
gactgcaatc aaaataggga cagggaagtt aggacttttg ataaatgacg atgagactat 8880

```
gcaatctgca gattacttga attatggaaa aataccgatt ttccgtggag tgattagagg   8940
gttagagacc aagagatggt cacgagtgac ttgtgtcacc aatgaccaaa tacccacttg   9000
tgctaatata atgagctcag tttccacaaa tgctctcacc gtagctcatt ttgctgagaa   9060
cccaatcaat gccatgatac agtacaatta ttttgggaca tttgctagac tcttgttgat   9120
gatgcatgat cctgctcttc gtcaatcatt gtatgaagtt caagataaga taccgggctt   9180
gcacagttct actttcaaat acgccatgtt gtatttggac ccttccattg gaggagtgtc   9240
gggcatgtct ttgtccaggt ttttgattag agccttccca gatcccgtaa cagaaagtct   9300
ctcattctgg agattcatcc atgtacatgc tcgaagtgag catctgaagg agatgagtgc   9360
agtatttgga aaccccgaga tagccaagtt tcgaataact cacatagaca agctagtaga   9420
agatccaacc tctctgaaca tcgctatggg aatgagtcca gcgaacttgt taaagactga   9480
ggttaaaaaa tgcttaatcg aatcaagaca aaccatcagg aaccaggtga ttaaggatgc   9540
aaccatatat ttgtatcatg aagaggatcg gctcagaagt ttcttatggt caataaatcc   9600
tctgttccct agatttttaa gtgaattcaa atcaggcact tttttgggag tcgcagacgg   9660
gctcatcagt ctatttcaaa attctcgtac tattcggaac tcctttaaga aaaagtatca   9720
tagggaattg gatgatttga ttgtgaggag tgaggtatcc tctttgacac atttagggaa   9780
acttcatttg agaaggggat catgtaaaat gtggacatgt tcagctactc atgctgacac   9840
attaagatac aaatcctggg gccgtacagt tattgggaca actgtacccc atccattaga   9900
aatgttgggt ccacaacatc gaaaagagac tccttgtgca ccatgtaaca catcagggtt   9960
caattatgtt tctgtgcatt gtccagacgg gatccatgac gtctttagtt cacggggacc  10020
attgcctgct tatctagggt ctaaaacatc tgaatctaca tctattttgc agccttggga  10080
aagggaaagc aaagtcccac tgattaaaag agctacacgt cttagagatg ctatctcttg  10140
gtttgttgaa cccgactcta aactagcaat gactatactt tctaacatcc actctttaac  10200
aggcgaagaa tggaccaaaa ggcagcatgg gttcaaaaga acagggtctg cccttcatag  10260
gttttcgaca tctcggatga gccatggtgg gttcgcatct cagagcactg cagcattgac  10320
caggttgatg gcaactacag acaccatgag ggatctggga gatcagaatt tcgacttttt  10380
attccaagca acgttgctct atgctcaaat taccaccact gttgcaagag acggatggat  10440
caccagttgt acagatcatt atcatattgc ctgtaagtcc tgtttgagac ccatagaaga  10500
gatcaccctg gactcaagta tggactacac gcccccagat gtatcccatg tgctgaagac  10560
atggaggaat ggggaaggtt cgtgggggaca agagataaaa cagatctatc ctttagaagg  10620
gaattggaag aatttagcac ctgctgagca atcctatcaa gtcggcagat gtataggttt  10680
tctatatgga gacttggcgt atagaaaatc tactcatgcc gaggacagtt ctctatttcc  10740
tctatctata caaggtcgta ttagaggtcg aggtttctta aaagggttgc tagacggatt  10800
aatgagagca agttgctgcc aagtaataca ccggagaagt ctggctcatt tgaagaggcc  10860
ggccaacgca gtgtacggag gtttgattta cttgattgat aaattgagtg tatcacctcc  10920
attcctttct cttactagat caggacctat tagagacgaa ttagaaacga ttccccacaa  10980
gatcccaacc tcctatccga caagcaaccg tgatatgggg gtgattgtca gaaattactt  11040
caaataccaa tgccgtctaa ttgaaaaggg aaaatacaga tcacattatt cacaattatg  11100
gttattctca gatgtcttat ccatagactt cattggacca ttctctattt ccaccaccct  11160
cttgcaaatc ctatacaagc catttttatc tgggaaagat aagaatgagt tgagagagct  11220
```

```
ggcaaatctt tcttcattgc taagatcagg agaggggtgg gaagacatac atgtgaaatt  11280

cttcaccaag gacatattat tgtgtccaga ggaaatcaga catgcttgca agttcgggat  11340

tgctaaggat aataataaag acatgagcta tccccttgg ggaagggaat ccagagggac  11400

aattacaaca atccctgttt attatacgac cacccttac ccaaagatgc tagagatgcc  11460

tccaagaatc caaaatcccc tgctgtccgg aatcaggttg ggccaattac caactggcgc  11520

tcattataaa attcggagta tattacatgg aatgggaatc cattacaggg acttcttgag  11580

ttgtggagac ggctccggag ggatgactgc tgcattacta cgagaaaatg tgcatagcag  11640

aggaatattc aatagtctgt tagaattatc agggtcagtc atgcgaggcg cctctcctga  11700

gcccccagt gccctagaaa ctttaggagg agataaatcg agatgtgtaa atggtgaaac  11760

atgttgggaa tatccatctg acttatgtga cccaaggact tgggactatt tcctccgact  11820

caaagcaggc ttggggcttc aaattgattt aattgtaatg gatatggaag ttcgggattc  11880

ttctactagc ctgaaaattg agacgaatgt tagaaattat gtgcaccgga ttttggatga  11940

gcaaggagtt ttaatctaca agacttatgg aacatatatt tgtgagagcg aaaagaatgc  12000

agtaacaatc cttggtccca tgttcaagac ggtcgactta gttcaaacag aatttagtag  12060

ttctcaaacg tctgaagtat atatggtatg taaaggtttg aagaaattaa tcgatgaacc  12120

caatcccgat tggtcttcca tcaatgaatc ctggaaaaac ctgtacgcat tccagtcatc  12180

agaacaggaa tttgccagag caaagaaggt tagtacatac tttaccttga caggtattcc  12240

ctcccaattc attcctgatc cttttgtaaa cattgagact atgctacaaa tattcggagt  12300

acccacgggt gtgtctcatg cggctgcctt aaaatcatct gatagacctg cagatttatt  12360

gaccattagc cttttttata tggcgattat atcgtattat aacatcaatc atatcagagt  12420

aggaccgata cctccgaacc ccccatcaga tggaattgca caaaatgtgg ggatcgctat  12480

aactggtata agcttttggc tgagtttgat ggagaaagac attccactat atcaacagtg  12540

tttagcagtt atccagcaat cattcccgat taggtgggag gctgtttcag taaaaggagg  12600

atacaagcag aagtggagta ctagaggtga tgggctccca aaagataccc gaatttcaga  12660

ctccttggcc ccaatcggga actggatcag atctctggaa ttggtccgaa accaagttcg  12720

tctaaatcca ttcaatgaga tcttgttcaa tcagctatgt cgtacagtgg ataatcattt  12780

gaaatggtca aatttgcgaa gaaacacagg aatgattgaa tggatcaata gacgaatttc  12840

aaaagaagac cggtctatac tgatgttgaa gagtgaccta cacgaggaaa actcttggag  12900

agattaaaaa atcatgagga gactccaaac tttaagtatg aaaaaaactt tgatccttaa  12960

gaccctcttg tggtttttat tttttatctg gttttgtggt cttcgt               13006
```

<210> SEQ ID NO 14
<211> LENGTH: 422
<212> TYPE: PRT
<213> ORGANISM: Vesicular stomatitis virus

<400> SEQUENCE: 14

```
Met Ser Val Thr Val Lys Arg Ile Ile Asp Asn Thr Val Ile Val Pro
1               5                   10                  15

Lys Leu Pro Ala Asn Glu Asp Pro Val Glu Tyr Pro Ala Asp Tyr Phe
            20                  25                  30

Arg Lys Ser Lys Glu Ile Pro Leu Tyr Ile Asn Thr Thr Lys Ser Leu
        35                  40                  45

Ser Asp Leu Arg Gly Tyr Val Tyr Gln Gly Leu Lys Ser Gly Asn Val
    50                  55                  60
```

```
Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
        115                 120                 125

Ala Asp Asp Lys Trp Leu Pro Leu Tyr Leu Leu Gly Leu Tyr Arg Val
    130                 135                 140

Gly Arg Thr Gln Met Pro Glu Tyr Arg Lys Lys Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
        195                 200                 205

Glu Cys Ala Ser Phe Arg Tyr Gly Thr Ile Val Ser Arg Phe Lys Asp
    210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
                245                 250                 255

Glu Met Val Gln Met Met Leu Pro Gly Gln Glu Ile Asp Lys Ala Asp
            260                 265                 270

Ser Tyr Met Pro Tyr Leu Ile Asp Phe Gly Leu Ser Ser Lys Ser Pro
        275                 280                 285

Tyr Ser Ser Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Cys Val Gly Asp
            340                 345                 350

Asn Lys Tyr Thr Pro Asp Asp Ser Thr Gly Gly Leu Thr Thr Asn Ala
        355                 360                 365

Pro Pro Gln Gly Arg Asp Val Val Glu Trp Leu Gly Trp Phe Glu Asp
    370                 375                 380

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
                405                 410                 415

Lys Ser Glu Phe Asp Lys
            420


<210> SEQ ID NO 15
<211> LENGTH: 265
<212> TYPE: PRT
<213> ORGANISM: Vesicular stomatitis virus

<400> SEQUENCE: 15

Met Asp Asn Leu Thr Lys Val Arg Glu Tyr Leu Lys Ser Tyr Ser Arg
```

```
1               5                   10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Lys Pro Ser Tyr Phe Gln Ala Ala Asp Asp Ser Asp Thr Glu Ser
    50                  55                  60

Glu Pro Glu Ile Glu Asp Asn Gln Gly Leu Tyr Ala Gln Asp Pro Glu
65                  70                  75                  80

Ala Glu Gln Val Glu Gly Phe Ile Gln Gly Pro Leu Asp Asp Tyr Ala
                85                  90                  95

Asp Glu Glu Val Asp Val Val Phe Thr Ser Asp Trp Lys Pro Pro Glu
            100                 105                 110

Leu Glu Ser Asp Glu His Gly Lys Thr Leu Arg Leu Thr Ser Pro Glu
        115                 120                 125

Gly Leu Ser Gly Glu Gln Lys Ser Gln Trp Leu Ser Thr Ile Lys Ala
    130                 135                 140

Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
        195                 200                 205

Pro Lys Lys Ala Ser Leu Gln Pro Leu Thr Ile Ser Leu Asp Glu Leu
    210                 215                 220

Phe Ser Ser Arg Gly Glu Phe Ile Ser Val Gly Gly Asp Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265


<210> SEQ ID NO 16
<211> LENGTH: 229
<212> TYPE: PRT
<213> ORGANISM: Vesicular stomatitis virus

<400> SEQUENCE: 16

Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110
```

```
Ser Ser Asn Leu Lys Ala Thr Pro Ala Val Leu Ala Asp Gln Gly Gln
        115                 120                 125

Pro Glu Tyr His Thr His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
    210                 215                 220

Ile Ser His Phe Lys
225


<210> SEQ ID NO 17
<211> LENGTH: 2109
<212> TYPE: PRT
<213> ORGANISM: Vesicular stomatitis virus

<400> SEQUENCE: 17

Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser
65                  70                  75                  80

Cys Gln Ala Asn Pro Ile Ser Thr Ser Gln Met His Lys Trp Met Gly
                85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255
```

```
Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
    290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
                325                 330                 335

Asp Gln Ile Met Ser Val Lys Thr Val Asp Leu Thr Leu Val Ile Tyr
            340                 345                 350

Gly Ser Phe Arg His Trp Gly His Pro Phe Ile Asp Tyr Tyr Thr Gly
        355                 360                 365

Leu Glu Lys Leu His Ser Gln Val Thr Met Lys Lys Asp Ile Asp Val
    370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
                405                 410                 415

Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
        435                 440                 445

Leu Ile Lys Cys Phe Glu Ile Pro Asp Leu Leu Asp Pro Ser Ile Ile
    450                 455                 460

Tyr Ser Asp Lys Ser His Ser Met Asn Arg Ser Glu Val Leu Lys His
465                 470                 475                 480

Val Arg Met Asn Pro Asn Thr Pro Ile Pro Ser Lys Lys Val Leu Gln
                485                 490                 495

Thr Met Leu Asp Thr Lys Ala Thr Asn Trp Lys Glu Phe Leu Lys Glu
            500                 505                 510

Ile Asp Glu Lys Gly Leu Asp Asp Asp Asp Leu Ile Ile Gly Leu Lys
        515                 520                 525

Gly Lys Glu Arg Glu Leu Lys Leu Ala Gly Arg Phe Phe Ser Leu Met
    530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
                565                 570                 575

Thr Ala Val Ile Lys Lys Met Leu Asp Ser Ser Ser Gly Gln Gly Leu
            580                 585                 590

Lys Ser Tyr Glu Ala Ile Cys Ile Ala Asn His Ile Asp Tyr Glu Lys
        595                 600                 605

Trp Asn Asn His Gln Arg Lys Leu Ser Asn Gly Pro Val Phe Arg Val
    610                 615                 620

Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
            660                 665                 670
```

```
Trp Gln Gly Gln Glu Gly Gly Leu Glu Gly Leu Arg Gln Lys Gly Trp
        675                 680                 685

Thr Ile Leu Asn Leu Leu Val Ile Gln Arg Glu Ala Lys Ile Arg Asn
    690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735

Leu Asn Gln Met Val Ser Asn Asn Glu Lys Ile Met Thr Ala Ile Lys
            740                 745                 750

Ile Gly Thr Gly Lys Leu Gly Leu Leu Ile Asn Asp Asp Glu Thr Met
        755                 760                 765

Gln Ser Ala Asp Tyr Leu Asn Tyr Gly Lys Ile Pro Ile Phe Arg Gly
    770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Leu Met
        835                 840                 845

Met His Asp Pro Ala Leu Arg Gln Ser Leu Tyr Glu Val Gln Asp Lys
    850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
            900                 905                 910

Phe Ile His Val His Ala Arg Ser Glu His Leu Lys Glu Met Ser Ala
        915                 920                 925

Val Phe Gly Asn Pro Glu Ile Ala Lys Phe Arg Ile Thr His Ile Asp
    930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
            980                 985                 990

Tyr His Glu Glu Asp Arg Leu Arg  Ser Phe Leu Trp Ser  Ile Asn Pro
        995                 1000                1005

Leu Phe  Pro Arg Phe Leu Ser  Glu Phe Lys Ser Gly  Thr Phe Leu
    1010                1015                1020

Gly Val  Ala Asp Gly Leu Ile  Ser Leu Phe Gln Asn  Ser Arg Thr
    1025                1030                1035

Ile Arg  Asn Ser Phe Lys Lys  Lys Tyr His Arg Glu  Leu Asp Asp
    1040                1045                1050

Leu Ile  Val Arg Ser Glu Val  Ser Ser Leu Thr His  Leu Gly Lys
    1055                1060                1065

Leu His  Leu Arg Arg Gly Ser  Cys Lys Met Trp Thr  Cys Ser Ala
    1070                1075                1080

Thr His  Ala Asp Thr Leu Arg  Tyr Lys Ser Trp Gly  Arg Thr Val
```

```
    1085                1090                1095

Ile Gly  Thr Thr Val Pro His  Pro Leu Glu Met Leu  Gly Pro Gln
    1100                1105                1110

His Arg  Lys Glu Thr Pro Cys  Ala Pro Cys Asn Thr  Ser Gly Phe
    1115                1120                1125

Asn Tyr  Val Ser Val His Cys  Pro Asp Gly Ile His  Asp Val Phe
    1130                1135                1140

Ser Ser  Arg Gly Pro Leu Pro  Ala Tyr Leu Gly Ser  Lys Thr Ser
    1145                1150                1155

Glu Ser  Thr Ser Ile Leu Gln  Pro Trp Glu Arg Glu  Ser Lys Val
    1160                1165                1170

Pro Leu  Ile Lys Arg Ala Thr  Arg Leu Arg Asp Ala  Ile Ser Trp
    1175                1180                1185

Phe Val  Glu Pro Asp Ser Lys  Leu Ala Met Thr Ile  Leu Ser Asn
    1190                1195                1200

Ile His  Ser Leu Thr Gly Glu  Glu Trp Thr Lys Arg  Gln His Gly
    1205                1210                1215

Phe Lys  Arg Thr Gly Ser Ala  Leu His Arg Phe Ser  Thr Ser Arg
    1220                1225                1230

Met Ser  His Gly Gly Phe Ala  Ser Gln Ser Thr Ala  Ala Leu Thr
    1235                1240                1245

Arg Leu  Met Ala Thr Thr Asp  Thr Met Arg Asp Leu  Gly Asp Gln
    1250                1255                1260

Asn Phe  Asp Phe Leu Phe Gln  Ala Thr Leu Leu Tyr  Ala Gln Ile
    1265                1270                1275

Thr Thr  Thr Val Ala Arg Asp  Gly Trp Ile Thr Ser  Cys Thr Asp
    1280                1285                1290

His Tyr  His Ile Ala Cys Lys  Ser Cys Leu Arg Pro  Ile Glu Glu
    1295                1300                1305

Ile Thr  Leu Asp Ser Ser Met  Asp Tyr Thr Pro Pro  Asp Val Ser
    1310                1315                1320

His Val  Leu Lys Thr Trp Arg  Asn Gly Glu Gly Ser  Trp Gly Gln
    1325                1330                1335

Glu Ile  Lys Gln Ile Tyr Pro  Leu Glu Gly Asn Trp  Lys Asn Leu
    1340                1345                1350

Ala Pro  Ala Glu Gln Ser Tyr  Gln Val Gly Arg Cys  Ile Gly Phe
    1355                1360                1365

Leu Tyr  Gly Asp Leu Ala Tyr  Arg Lys Ser Thr His  Ala Glu Asp
    1370                1375                1380

Ser Ser  Leu Phe Pro Leu Ser  Ile Gln Gly Arg Ile  Arg Gly Arg
    1385                1390                1395

Gly Phe  Leu Lys Gly Leu Leu  Asp Gly Leu Met Arg  Ala Ser Cys
    1400                1405                1410

Cys Gln  Val Ile His Arg Arg  Ser Leu Ala His Leu  Lys Arg Pro
    1415                1420                1425

Ala Asn  Ala Val Tyr Gly Gly  Leu Ile Tyr Leu Ile  Asp Lys Leu
    1430                1435                1440

Ser Val  Ser Pro Pro Phe Leu  Ser Leu Thr Arg Ser  Gly Pro Ile
    1445                1450                1455

Arg Asp  Glu Leu Glu Thr Ile  Pro His Lys Ile Pro  Thr Ser Tyr
    1460                1465                1470

Pro Thr  Ser Asn Arg Asp Met  Gly Val Ile Val Arg  Asn Tyr Phe
    1475                1480                1485
```

```
Lys Tyr  Gln Cys Arg Leu Ile  Glu Lys Gly Lys Tyr  Arg Ser His
    1490                 1495                 1500

Tyr Ser  Gln Leu Trp Leu Phe  Ser Asp Val Leu Ser  Ile Asp Phe
    1505                 1510                 1515

Ile Gly  Pro Phe Ser Ile Ser  Thr Thr Leu Leu Gln  Ile Leu Tyr
    1520                 1525                 1530

Lys Pro  Phe Leu Ser Gly Lys  Asp Lys Asn Glu Leu  Arg Glu Leu
    1535                 1540                 1545

Ala Asn  Leu Ser Ser Leu Leu  Arg Ser Gly Glu Gly  Trp Glu Asp
    1550                 1555                 1560

Ile His  Val Lys Phe Phe Thr  Lys Asp Ile Leu Leu  Cys Pro Glu
    1565                 1570                 1575

Glu Ile  Arg His Ala Cys Lys  Phe Gly Ile Ala Lys  Asp Asn Asn
    1580                 1585                 1590

Lys Asp  Met Ser Tyr Pro Pro  Trp Gly Arg Glu Ser  Arg Gly Thr
    1595                 1600                 1605

Ile Thr  Thr Ile Pro Val Tyr  Tyr Thr Thr Thr Pro  Tyr Pro Lys
    1610                 1615                 1620

Met Leu  Glu Met Pro Pro Arg  Ile Gln Asn Pro Leu  Leu Ser Gly
    1625                 1630                 1635

Ile Arg  Leu Gly Gln Leu Pro  Thr Gly Ala His Tyr  Lys Ile Arg
    1640                 1645                 1650

Ser Ile  Leu His Gly Met Gly  Ile His Tyr Arg Asp  Phe Leu Ser
    1655                 1660                 1665

Cys Gly  Asp Gly Ser Gly Gly  Met Thr Ala Ala Leu  Leu Arg Glu
    1670                 1675                 1680

Asn Val  His Ser Arg Gly Ile  Phe Asn Ser Leu Leu  Glu Leu Ser
    1685                 1690                 1695

Gly Ser  Val Met Arg Gly Ala  Ser Pro Glu Pro Pro  Ser Ala Leu
    1700                 1705                 1710

Glu Thr  Leu Gly Gly Asp Lys  Ser Arg Cys Val Asn  Gly Glu Thr
    1715                 1720                 1725

Cys Trp  Glu Tyr Pro Ser Asp  Leu Cys Asp Pro Arg  Thr Trp Asp
    1730                 1735                 1740

Tyr Phe  Leu Arg Leu Lys Ala  Gly Leu Gly Leu Gln  Ile Asp Leu
    1745                 1750                 1755

Ile Val  Met Asp Met Glu Val  Arg Asp Ser Ser Thr  Ser Leu Lys
    1760                 1765                 1770

Ile Glu  Thr Asn Val Arg Asn  Tyr Val His Arg Ile  Leu Asp Glu
    1775                 1780                 1785

Gln Gly  Val Leu Ile Tyr Lys  Thr Tyr Gly Thr Tyr  Ile Cys Glu
    1790                 1795                 1800

Ser Glu  Lys Asn Ala Val Thr  Ile Leu Gly Pro Met  Phe Lys Thr
    1805                 1810                 1815

Val Asp  Leu Val Gln Thr Glu  Phe Ser Ser Ser Gln  Thr Ser Glu
    1820                 1825                 1830

Val Tyr  Met Val Cys Lys Gly  Leu Lys Lys Leu Ile  Asp Glu Pro
    1835                 1840                 1845

Asn Pro  Asp Trp Ser Ser Ile  Asn Glu Ser Trp Lys  Asn Leu Tyr
    1850                 1855                 1860

Ala Phe  Gln Ser Ser Glu Gln  Glu Phe Ala Arg Ala  Lys Lys Val
    1865                 1870                 1875
```

-continued

```
Ser Thr  Tyr Phe Thr Leu Thr  Gly Ile Pro Ser Gln  Phe Ile Pro
    1880                 1885                 1890

Asp Pro  Phe Val Asn Ile Glu  Thr Met Leu Gln Ile  Phe Gly Val
    1895                 1900                 1905

Pro Thr  Gly Val Ser His Ala  Ala Ala Leu Lys Ser  Ser Asp Arg
    1910                 1915                 1920

Pro Ala  Asp Leu Leu Thr Ile  Ser Leu Phe Tyr Met  Ala Ile Ile
    1925                 1930                 1935

Ser Tyr  Tyr Asn Ile Asn His  Ile Arg Val Gly Pro  Ile Pro Pro
    1940                 1945                 1950

Asn Pro  Pro Ser Asp Gly Ile  Ala Gln Asn Val Gly  Ile Ala Ile
    1955                 1960                 1965

Thr Gly  Ile Ser Phe Trp Leu  Ser Leu Met Glu Lys  Asp Ile Pro
    1970                 1975                 1980

Leu Tyr  Gln Gln Cys Leu Ala  Val Ile Gln Gln Ser  Phe Pro Ile
    1985                 1990                 1995

Arg Trp  Glu Ala Val Ser Val  Lys Gly Gly Tyr Lys  Gln Lys Trp
    2000                 2005                 2010

Ser Thr  Arg Gly Asp Gly Leu  Pro Lys Asp Thr Arg  Thr Ser Asp
    2015                 2020                 2025

Ser Leu  Ala Pro Ile Gly Asn  Trp Ile Arg Ser Leu  Glu Leu Val
    2030                 2035                 2040

Arg Asn  Gln Val Arg Leu Asn  Pro Phe Asn Glu Ile  Leu Phe Asn
    2045                 2050                 2055

Gln Leu  Cys Arg Thr Val Asp  Asn His Leu Lys Trp  Ser Asn Leu
    2060                 2065                 2070

Arg Arg  Asn Thr Gly Met Ile  Glu Trp Ile Asn Arg  Arg Ile Ser
    2075                 2080                 2085

Lys Glu  Asp Arg Ser Ile Leu  Met Leu Lys Ser Asp  Leu His Glu
    2090                 2095                 2100

Glu Asn  Ser Trp Arg Asp
    2105
```